United States Patent [19]
Weldon et al.

[11] Patent Number: 5,419,765
[45] Date of Patent: May 30, 1995

[54] WOUND TREATING DEVICE AND METHOD FOR TREATING WOUNDS

[75] Inventors: Thomas D. Weldon, Gainesville; Charles E. Larsen, Cumming; Jonathan J. Rosen, Alpharetta, all of Ga.

[73] Assignee: Novoste Corporation, Norcross, Ga.

[21] Appl. No.: 197,123

[22] Filed: Feb. 16, 1994

Related U.S. Application Data

[63] Continuation-in-part of Ser. No. 899,507, Jun. 16, 1992, Pat. No. 5,330,446, which is a continuation-in-part of Ser. No. 634,406, Dec. 27, 1990, Pat. No. 5,129,882.

[51] Int. Cl.$^6$ .............................. A61M 29/00
[52] U.S. Cl. ...................... 604/96; 606/213; 604/52; 604/57; 604/60
[58] Field of Search .............. 604/11, 27, 38, 46, 604/47, 52, 57, 59–60, 93, 96, 171, 173, 218, 235, 285–287, 310–311, 890.1; 606/194, 213

[56] References Cited

U.S. PATENT DOCUMENTS

| | | |
|---|---|---|
| 682,090 | 9/1901 | Lee . |
| 3,833,003 | 9/1974 | Taricco .................. 128/347 |
| 4,271,839 | 6/1981 | Fogarty et al. ............. 128/344 |
| 4,471,779 | 9/1984 | Antoshkiw et al. .......... 128/325 |
| 4,545,367 | 10/1985 | Tucci ..................... 128/1 R |
| 4,582,181 | 4/1986 | Samson ................. 128/348.1 |
| 4,638,803 | 1/1987 | Rand ..................... 128/325 |
| 4,654,025 | 3/1987 | Cassou et al. ................ 604/55 |
| 4,735,616 | 4/1988 | Eibl et al. .................. 604/191 |
| 4,744,364 | 5/1988 | Kensey ................... 128/334 R |
| 4,779,611 | 10/1988 | Grooters et al. ................ 128/4 |
| 4,852,568 | 8/1989 | Kensey .................... 128/325 |
| 4,890,612 | 1/1990 | Kensey .................... 606/213 |
| 4,900,303 | 2/1990 | Lemelson ................... 604/54 |
| 4,911,163 | 3/1990 | Fina ....................... 606/127 |
| 5,021,059 | 6/1991 | Kensey et al. .............. 606/213 |
| 5,062,829 | 11/1991 | Pryor et al. ................. 604/57 |
| 5,108,421 | 4/1992 | Fowler .................... 606/213 |
| 5,192,300 | 3/1993 | Fowler .................... 606/213 |
| 5,199,951 | 4/1993 | Spears ..................... 604/96 |
| 5,304,117 | 4/1994 | Wilk ....................... 604/49 |

FOREIGN PATENT DOCUMENTS

| | | |
|---|---|---|
| 0210160 | 1/1987 | European Pat. Off. . |
| 0241038 | 10/1987 | European Pat. Off. . |
| 0367516 | 5/1990 | European Pat. Off. . |
| WO89/11301 | 11/1989 | WIPO . |
| WO90/14796 | 12/1990 | WIPO . |

*Primary Examiner*—Corrine Maglione
*Attorney, Agent, or Firm*—Cook, Egan, McFarron & Manzo

[57] ABSTRACT

A wound treating device is disclosed which is adapted to treat wounds, and particularly to enhance clotting of wounds in blood vessels. The wound treating device includes an elongated tube with proximal and distal end portions and comprising at least two lumens extending therebetween. One of the lumens is attached to receive a flow control device partially positioned within the blood vessel for providing local flow control at the wound site. Inflatable means, such as a flexible membrane, is carried generally adjacent to the distal end portion and is movable between inflated and retracted positions.

32 Claims, 17 Drawing Sheets

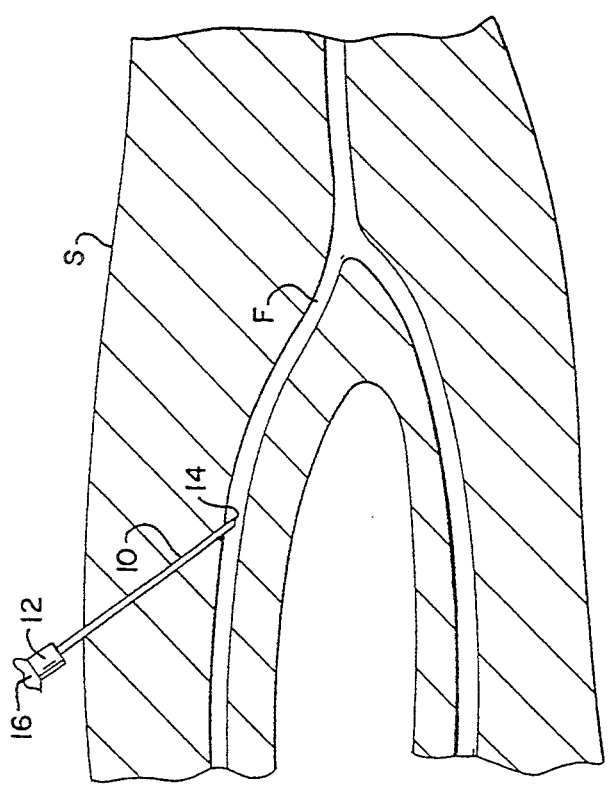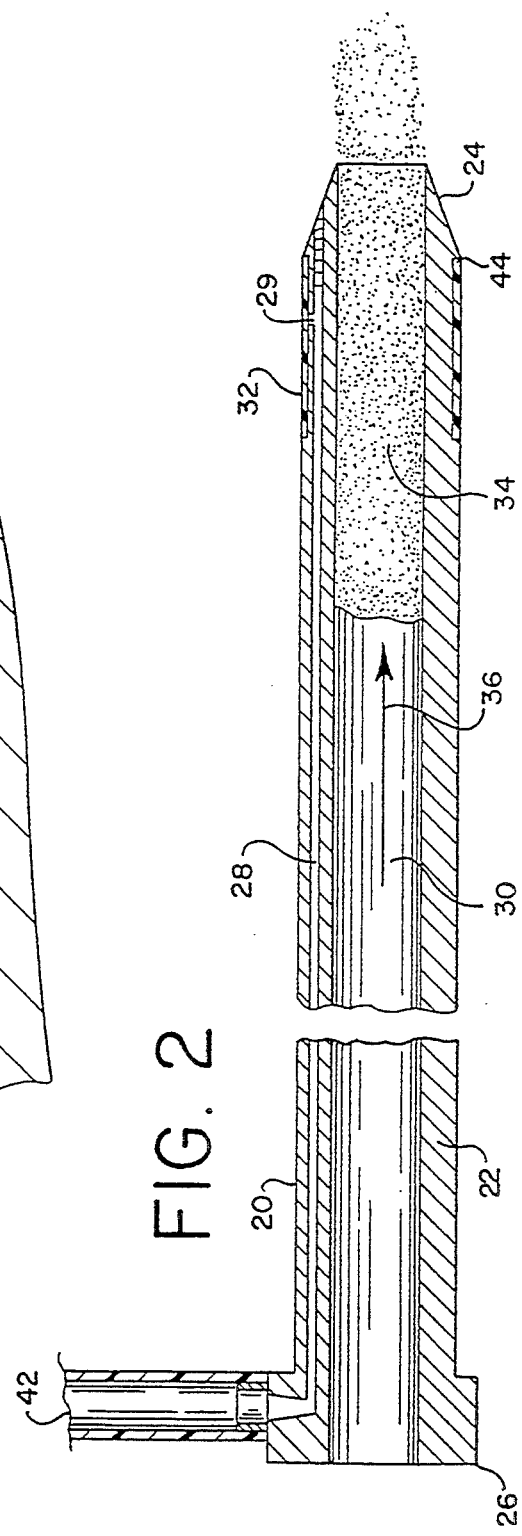

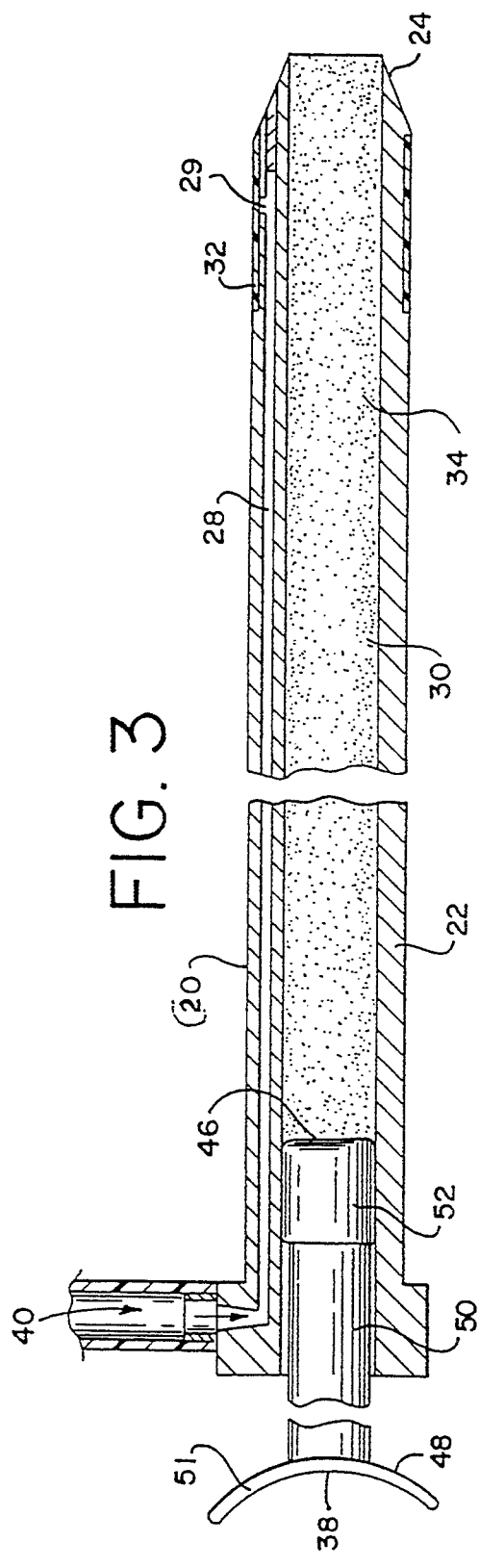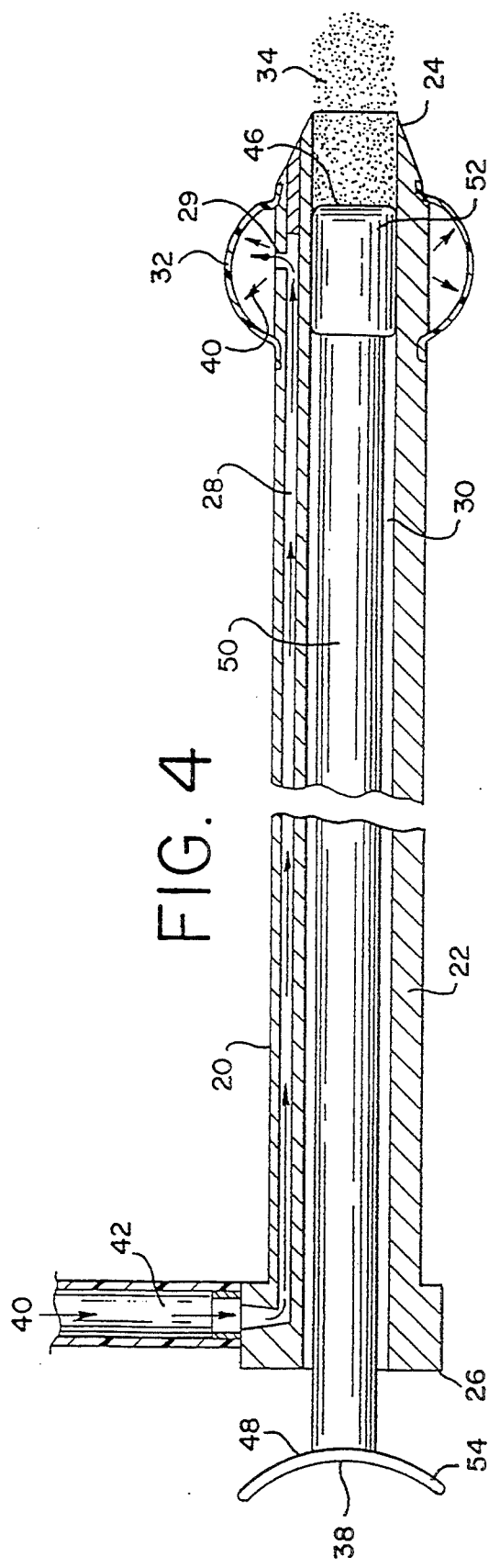

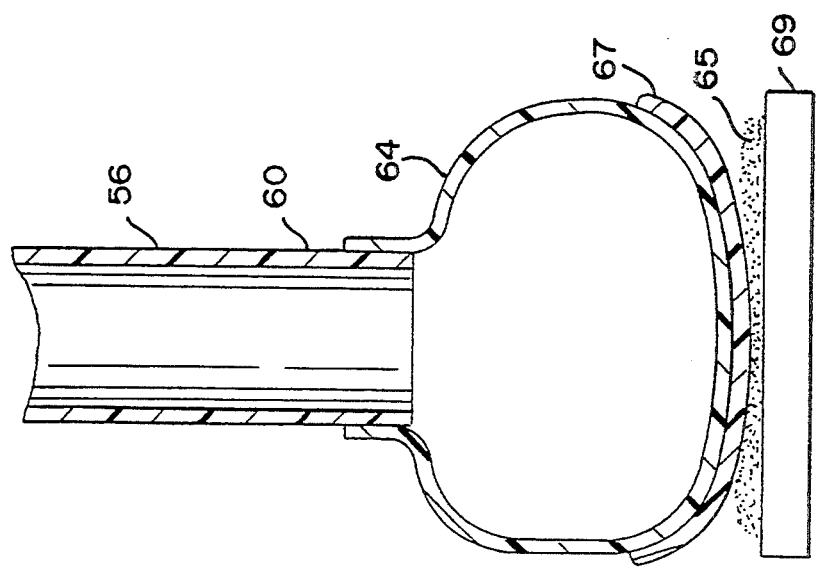
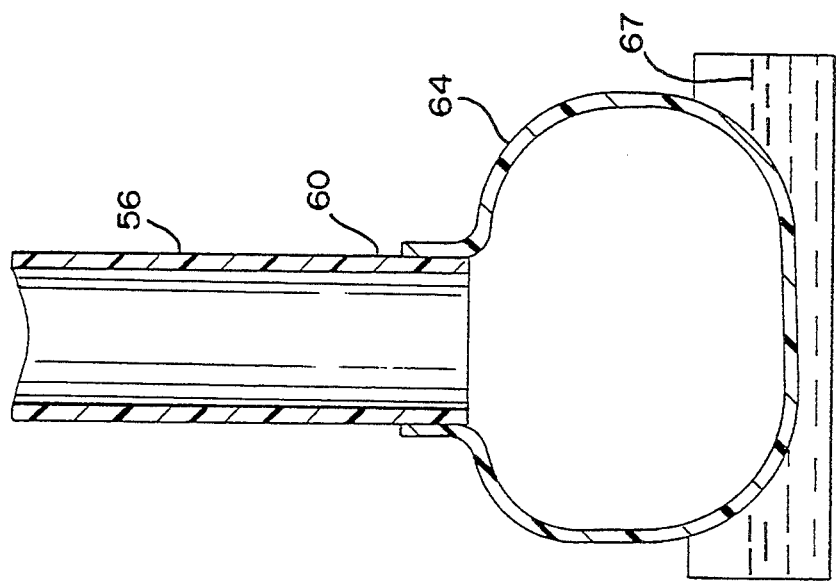
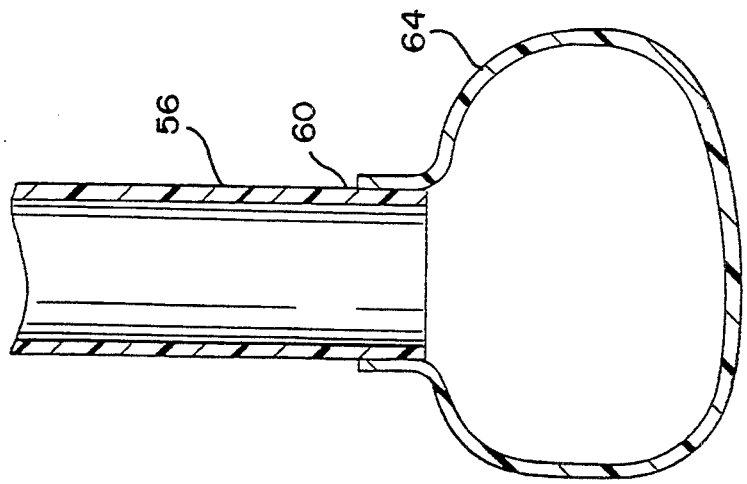

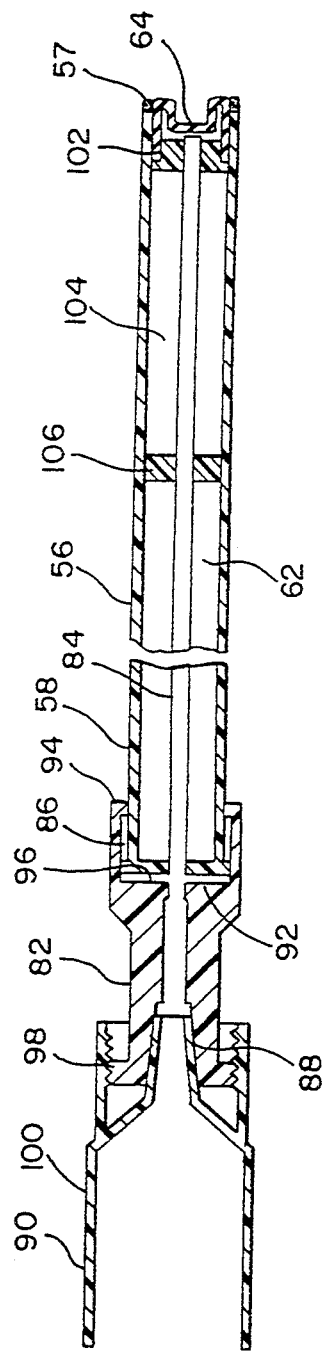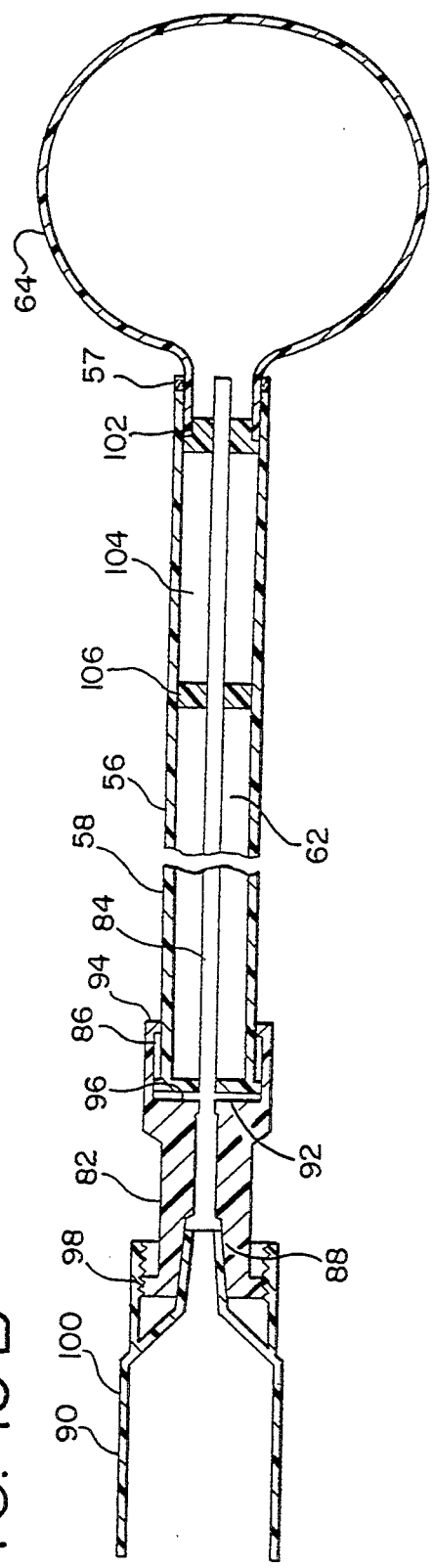

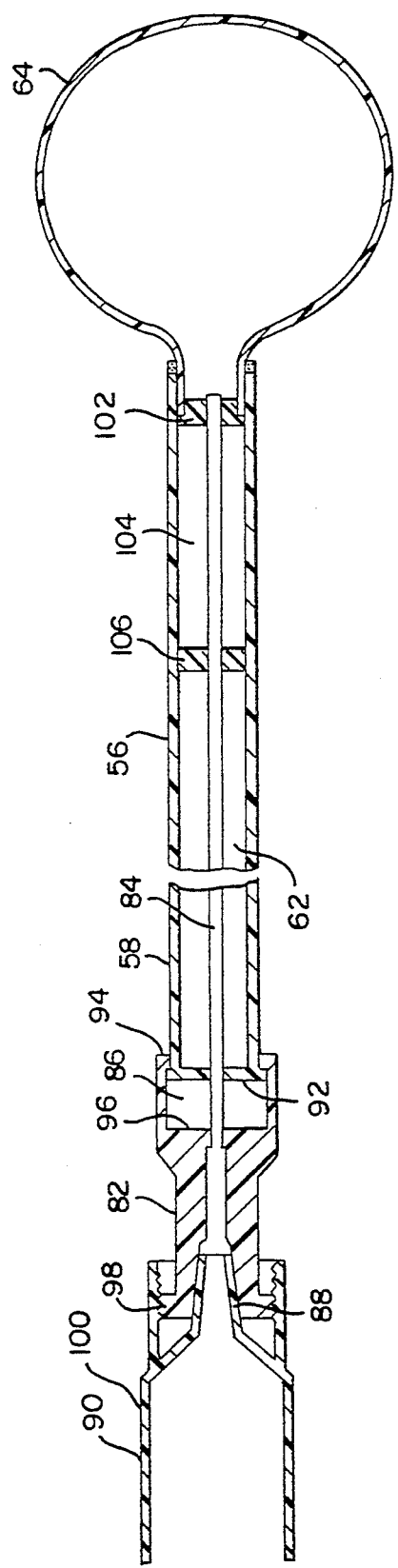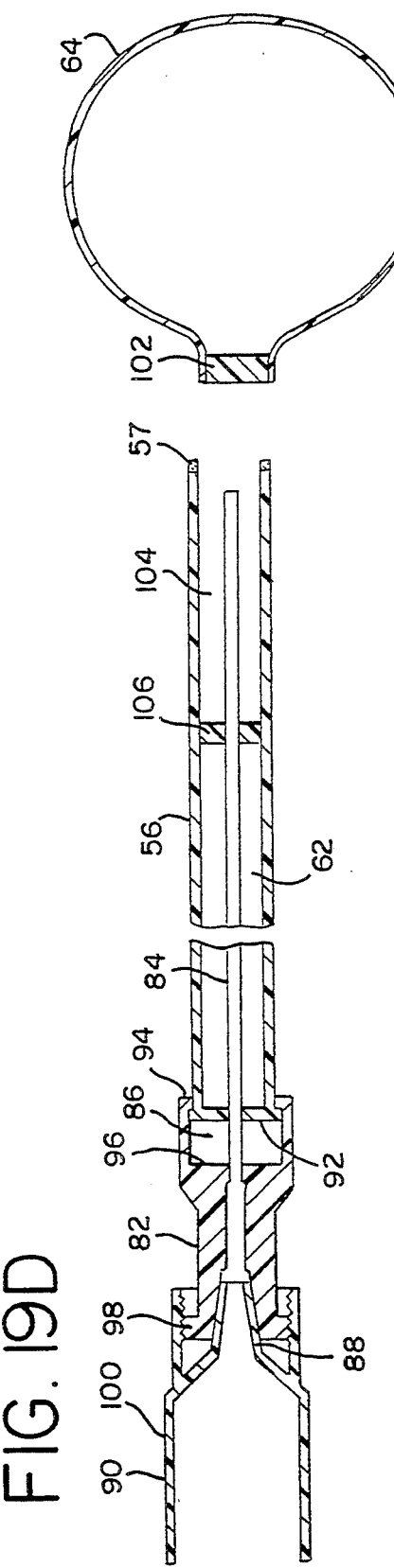

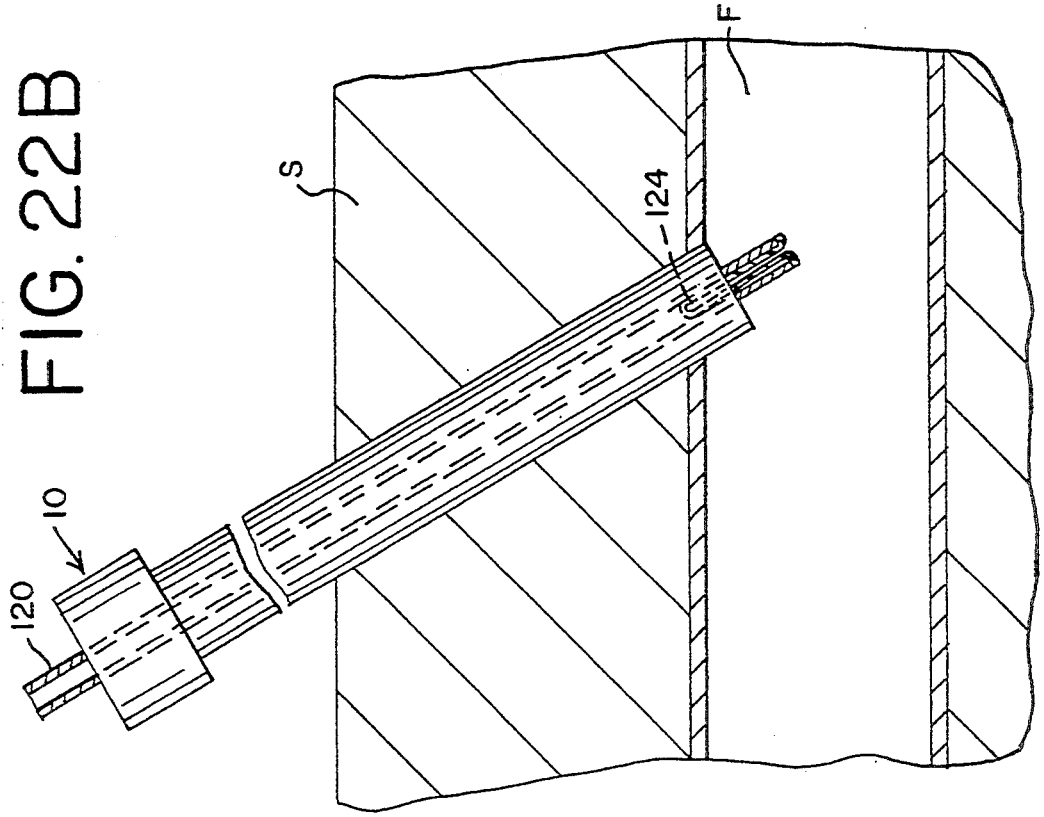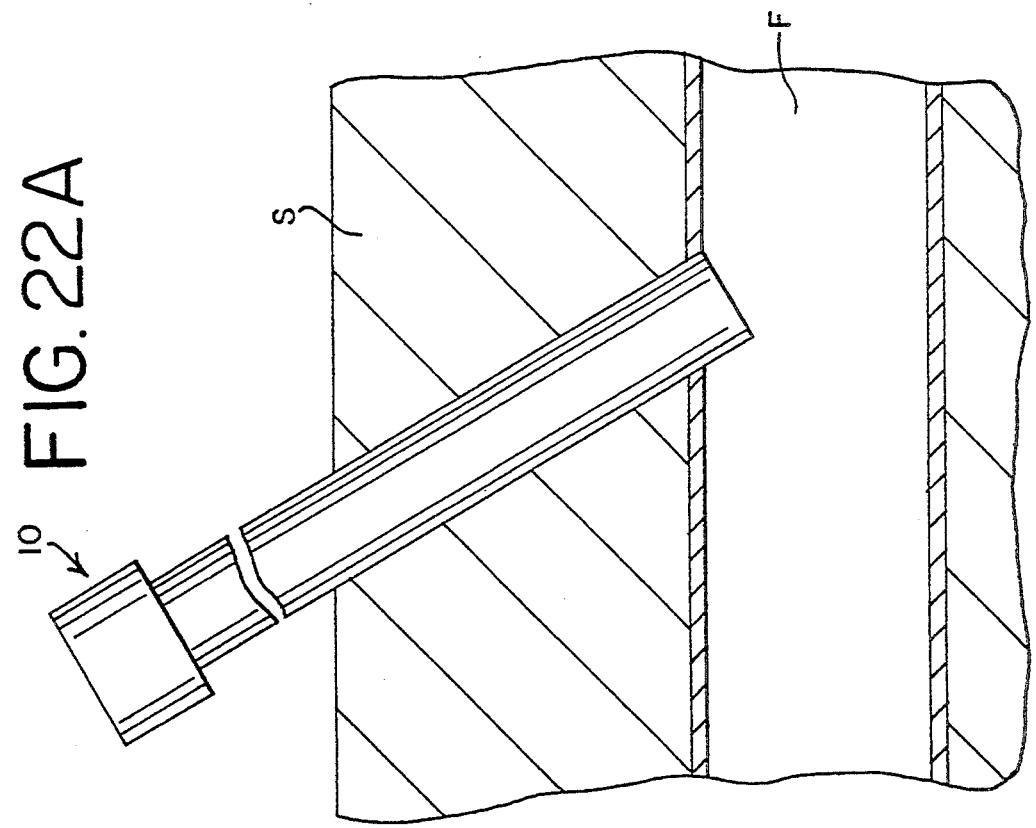

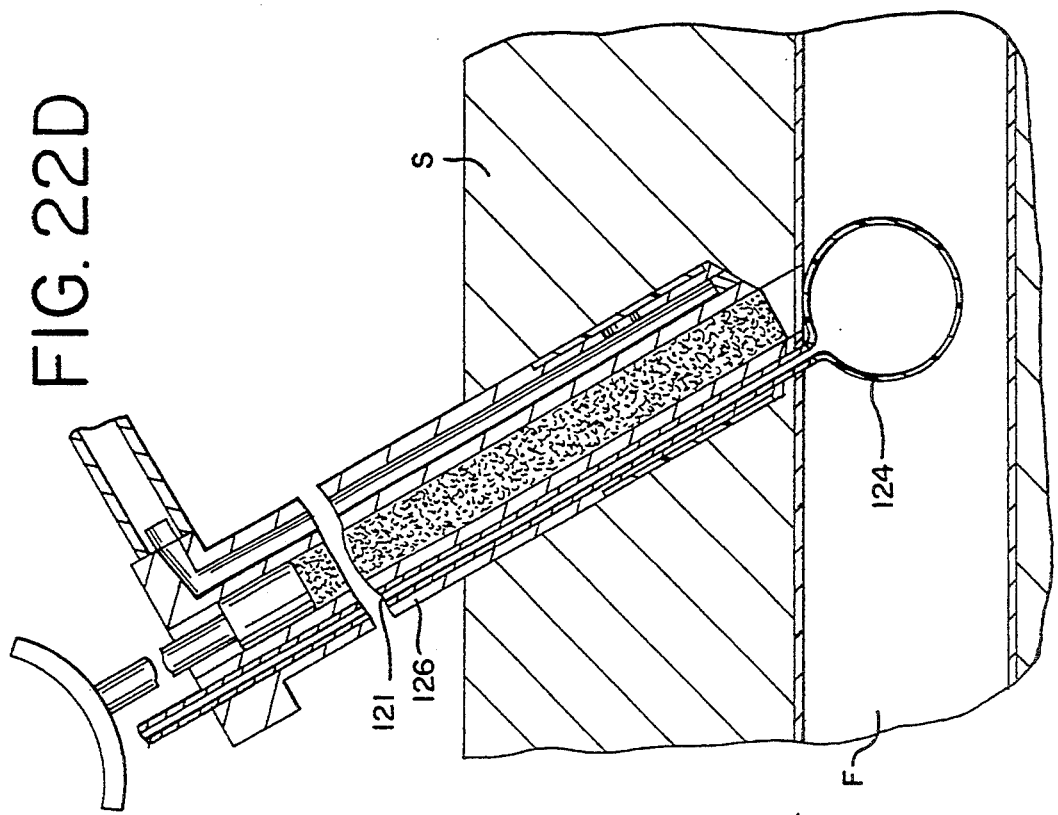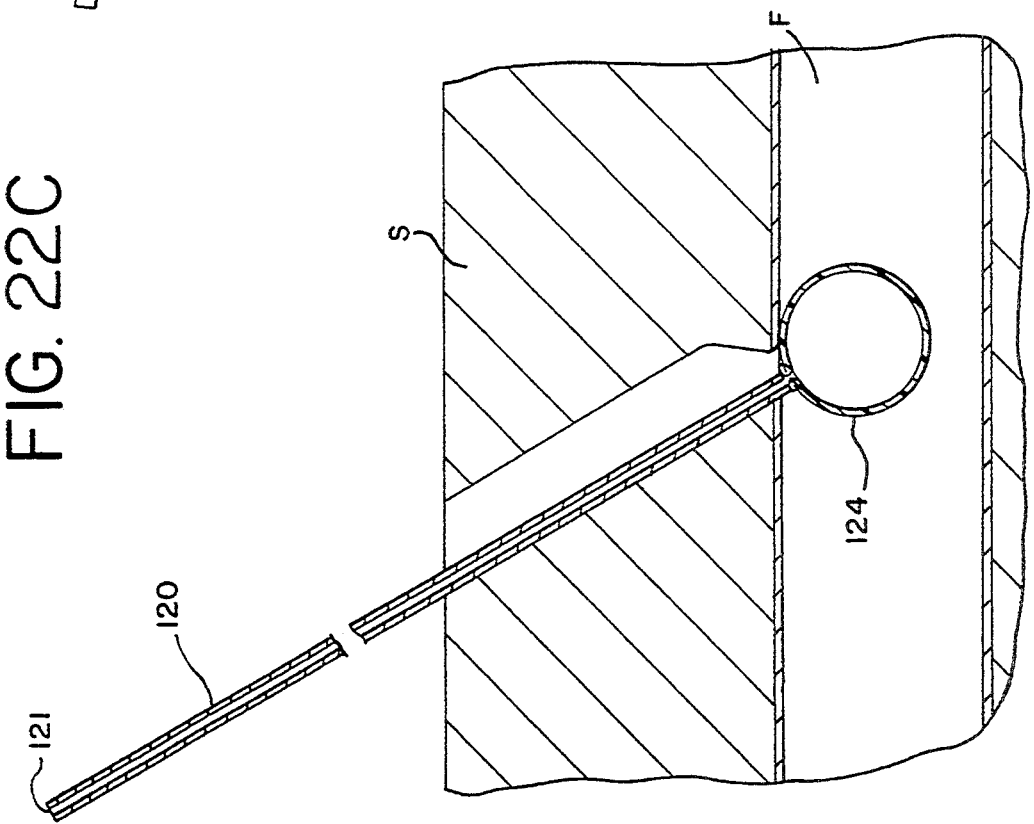

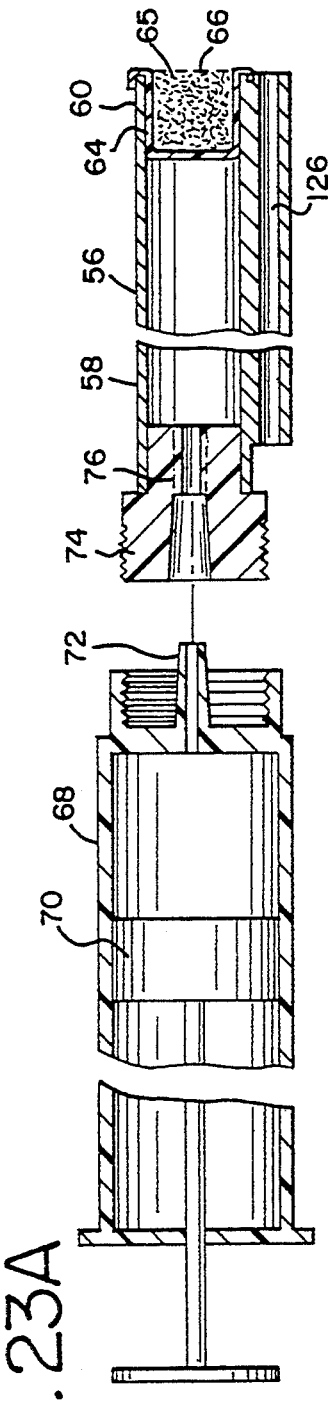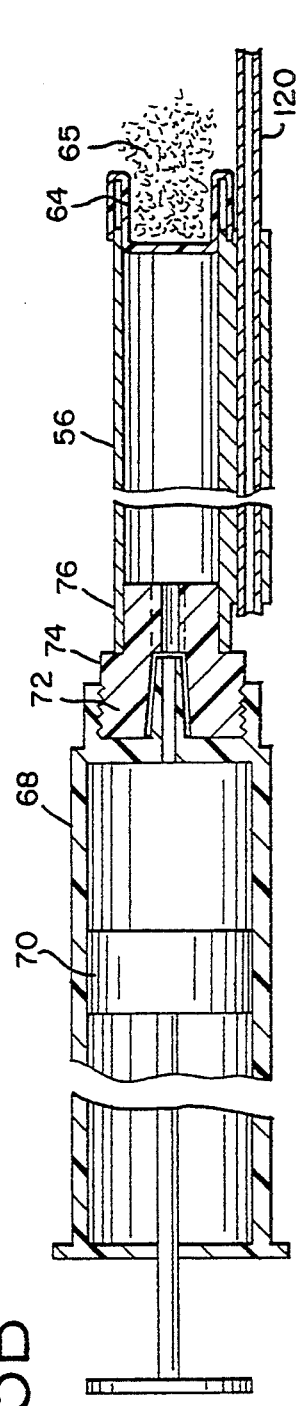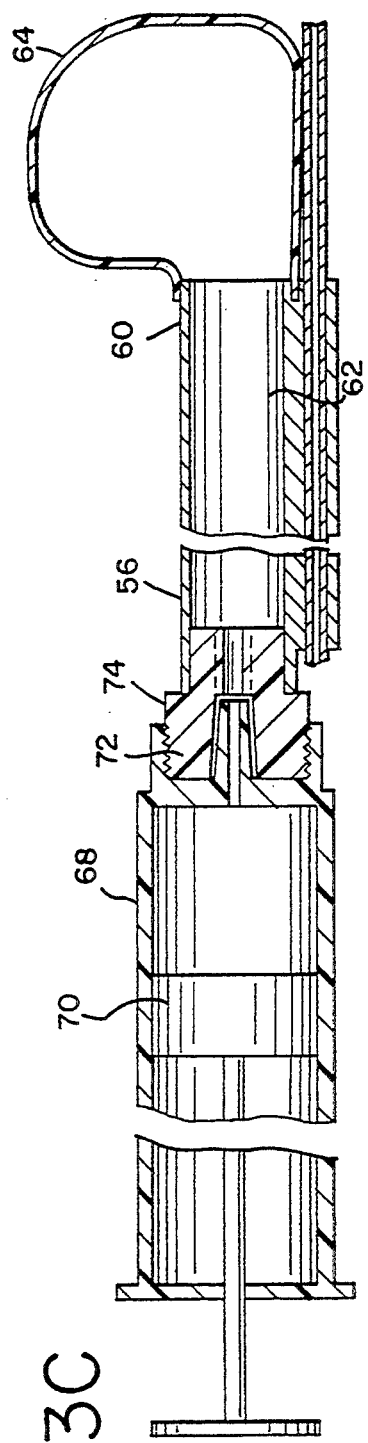

WOUND TREATING DEVICE AND METHOD FOR TREATING WOUNDS

This is a continuation-in-part of application Ser. No. 899,507, filed Jun. 16, 1992, now U.S. Pat. No. 5,330,446, which is a continuation-in-part of application Ser. No. 634,406, filed Dec. 27, 1990, which issued as U.S. Pat. No. 5,129,882 on Jul. 14, 1992.

BACKGROUND

The present invention relates, in general, to devices and methods for stopping an undesirable flow of fluid between two contiguous tissue samples, such as bleeding from a blood vessel after removal of a medical device, catheter system, or the like. More particularly, the present invention concerns a novel wound treating device which includes means for depositing a treating agent at a wound or aperture between two contiguous tissue areas, such as depositing a clotting or hemostatic agent at the opening in a blood vessel or the like following removal of a medical device or instrument therefrom. The present invention also concerns a novel method for using such a wound treating device.

Many medical procedures, including both therapeutic and diagnostic procedures, often require access between two contiguous tissue areas, such as through the skin and into the vascular system of the patient. As an example, although various means may be used to obtain access into a vein or artery, typically access is obtained by inserting a cannula or catheter (called an introducer catheter or sheath) through the skin and into the selected blood vessel. A medical or diagnostic instrument, such as a guide wire, guiding catheter, balloon angioplasty device, atherectomy device, or the like is then inserted into the vascular system through the introducer catheter.

Depending on the procedure, to permit the insertion of the diagnostic or therapeutic device therethrough, the introducer sheath must be of relatively large diameter. This, of course, results in a relatively large hole or aperture in the vessel wall. After the medical procedure is completed, however, this opening must be closed, and bleeding from the blood vessel stopped.

A common technique to stop such bleeding, as in cardiac balloon angioplasty procedures, is for a nurse or technician to manually apply direct and continuous pressure on the opening in the blood vessel until the blood clots. This may require an hour or more of medical personnel time. Unfortunately, when this procedure is utilized, there is also a significant chance that movement by the patient will reopen the opening and that it will begin bleeding again, resulting in a hematoma or other complications. Because of the risk of bleeding, patients are usually required to remain overnight in the hospital for rest and observation, thus greatly increasing the cost of the overall procedure.

One prior device for stopping bleeding from an aperture in a blood vessel is a type of expandable plug. The plug is pushed through the opening into the blood vessel and into the blood stream. Once in the blood stream, it expands. The expanded plug is then pulled back against the aperture where, because of its expanded size, it plugs the opening. Such a device may work satisfactorily, but requires inserting and leaving a foreign object in the vessel. It is usually medically preferable to avoid inserting and leaving objects in a vessel.

Accordingly, it is a general object of the present invention to provide a wound treating device, as well as a method for using such device, which are particularly useful in treating and assisting in treating wounds such as vascular wounds that result from insertion of a medical device, such as a catheter, and which do not suffer from the drawbacks described above.

SUMMARY OF THE INVENTION

The wound treating device of the present invention is adapted to be positioned adjacent to an aperture or other wound in a blood vessel for the purpose of treating and, in particular, promoting clotting and healing of the aperture or other wound. The wound treating device comprises an elongated tube having a proximal end portion, a distal end portion, and preferably at least two lumens extending therebetween. One of the lumens is adapted to receive a flow control device which may be partially positioned within a blood vessel for providing local control of the flow of blood from the vessel aperture. An inflatable means, in the form of a flexible inflatable membrane located generally adjacent to the distal end portion, is cooperatively associated with the other lumen and is movable between a retracted position and an inflated position to form a balloon-like projection generally adjacent to the distal end.

To enhance clotting or healing of the vessel aperture, various other aspects of the present invention may be employed. For example, the membrane of the wound treating device may have a clot inducing surface, may have a treating material on its surface, or may actually expel a treating material from the lumen of the tube as it is inflated. Alternatively, another lumen may be provided in the elongated tube from which or through which a treating material is discharged.

The flow control device of the present invention, referred to above, preferably has a tubular portion including proximal and distal end portions and a membrane attached to the distal end portion. The membrane is inflatable to form a balloon-like projection, which may be used to help control the flow of blood from the vessel aperture and to enhance clotting as described more fully below.

In operation, treatment of a wound, such as aiding in the clotting of an aperture in a blood vessel, may be performed utilizing a wound treating device as described above, with or without an introducer sheath or cannula. When an introducer sheath is used, following the removal of the diagnostic or therapeutic device such as a catheter or atherectomy device, the flow control device is inserted through the sheath into the vessel aperture. The membrane of the flow control device is then inflated and pulled back to occlude the aperture and restrict the flow of blood from the vessel. The introducer sheath may next be retracted from the wound at least until the distal end of the sheath is in the proximity of but spaced from the wound site. The wound treating device is now advanced along the tube of the flow control device until the wound treating device extends beyond the distal end of the sheath and is adjacent to the wound site. The inflatable means at the distal end of the wound treating device is then inflated, serving to hold the distal end adjacent to the wound and to further restrict blood flow when the membrane of the flow control device is deflated. The inflatable means may also be adapted to apply a treating or clotting agent associated with the membrane. If it has not been done so already, a treating or clotting agent may now be administered through the tube of the wound treating device. The flow control device helps prevent flow of clotting agent into the vessel itself. After sufficient time has elapsed, the membrane of the wound treating device, and/or the flow control device, if not already removed, are deflated and retracted, leaving no substantial foreign matter in the vessel of the patient. The same procedure may also be used without an introducer sheath.

These and additional features and advantages of the present invention will become more apparent from the following detailed description of the invention, as exemplified in the accompanying drawings.

BRIEF DESCRIPTION OF THE DRAWINGS

FIG. 1 is a fragmentary diagrammatic view of a sheath introducer extending through the skin into a femoral artery of a patient.

FIG. 2 is an enlarged cross-sectional view of the proximal and distal end portions of a wound treating or clotting device of the present invention with a means for dispensing a clotting agent shown diagrammatically.

FIG. 3 is a cross-sectional view showing the proximal and distal ends of one embodiment of the wound treating or clotting device of the present invention utilizing a plunger for dispensing the clotting agent and containing a quantity of clotting agent.

FIG. 4 is a cross-sectional view of the wound treating or clotting device of FIG. 3 showing the inflatable retention means inflated and a plunger ejecting the clotting agent from the device's distal end.

FIGS. 16A–C show steps in applying a release agent and a treating agent to the surface of the membrane.

FIGS. 19A–D show an alternate embodiment of the wound treating device, in sequential operative positions, having a detachable membrane.

FIGS. 22A–F show, in sequential operative positions, the alternate embodiment of the wound treating device depicted in FIG. 21 with the flow control device depicted in FIG. 20.

FIGS. 23A–C show an enlarged cross-sectional view, in sequential operative positions, of a further alternative wound treating device for use with the flow control device of FIG. 20.

DETAILED DESCRIPTION OF THE INVENTION

Figure 5:
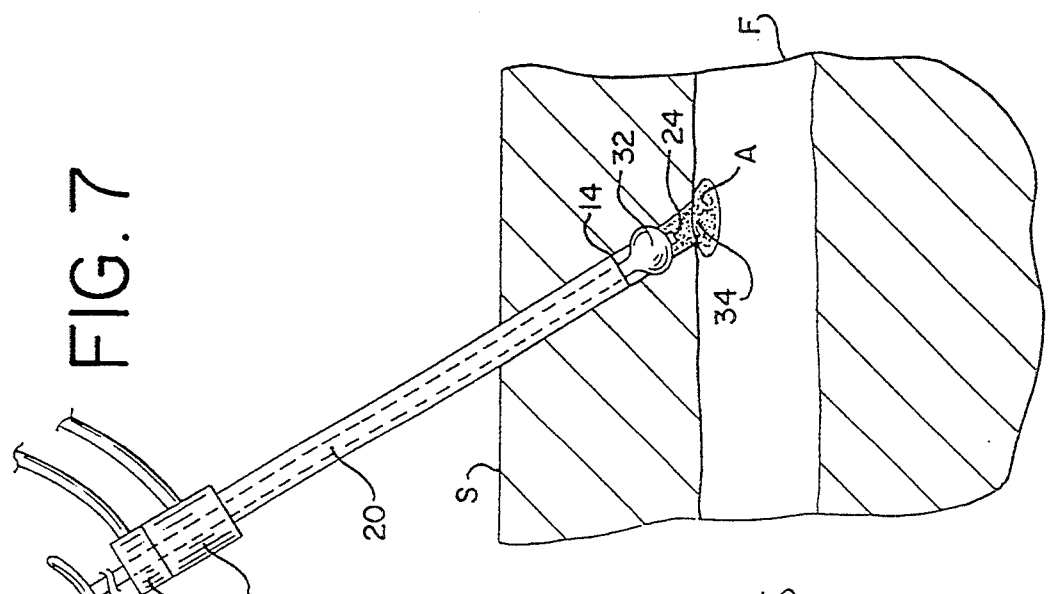
FIG. 5 is a side view of a sheath introducer which has been introduced through the skin and into a blood vessel.

FIG. 1 is a partial diagrammatic representation of a sheath introducer 10 which has been advanced through the skin surface S into a femoral artery F of a living patient. The sheath introducer 10 is shown in the femoral artery F for purposes of illustration only and not for purposes of limitation. It is understood that a sheath introducer can also be used in accessing other arteries, veins, or blood vessels, or in communicating between other contiguous tissue areas of a patient's body.

As shown in the exemplary procedure of FIG. 1, the sheath introducer 10 is initially advanced through a patient's skin and into the artery F. The sheath introducer 10 has a resealable valve 12 located at its proximal end 16, as is well known in the medical field. In the typical procedure, some type of medical device, for example, a guiding catheter, an angioplasty device, or the like, is inserted into the sheath introducer through the valve and advanced into the artery and then to the location of the procedure. After the medical device has been used, it is withdrawn from the artery and the sheath introducer. The sheath introducer 10 must then be removed from the artery F. This, of course, leaves an aperture or opening in the artery F (See FIGS. 6 and 7). To assist in stopping bleeding from the opening in the artery, the wound treating device of the present invention may be utilized.

FIGS. 2, 3, and 4 show, in an enlarged view, various embodiments of the wound treating or clotting device of the present invention. With reference to these figures, the wound treating device 20 of the present invention comprises a tube, generally at 22, with a distal end portion generally at 24 and a proximal end portion generally at 26. A relatively large second lumen 30 and a smaller inflation lumen 28 extend between the proximal end 26 to the distal end 24 of the tube 22. The second lumen 30 is open at the distal end, and the distal end of the inflation lumen is sealed closed.

The tube may be formed by extrusion from a suitable plastic such as nylon, polypropylene, or the like, although the present invention is not limited by the method of manufacture or the type of material, and injection molding or other materials could be used where feasible. The plastic material utilized in the manufacture of the tube should in any event, be sufficiently stiff so as to be capable of being advanced through an introducer cannula or sheath introducer, but not so stiff that it will cause damage to tissue.

The inflation lumen 28 extends fully between the proximal end and distal ends of the tube 22. As noted above, the inflation lumen is sealed at the distal end and carries a valve (not shown) at the other end, through which an inflation fluid, such as sterile water, may be injected. Such a valve is well known in medical product design and thus it will not be described in detail here. The diameter of the inflation lumen may vary, depending on the particular application. Typically, however, the diameter should be sufficiently large to permit ready inflation of the inflatable means.

In the embodiment of the wound treating device shown in FIGS. 3 and 4, an inflatable means 32 is located on the distal end 24 of the tube 22 for retention of the tube at the desired location and/or for applying a wound treating agent, although other types or forms of retention means may also be used for retaining the distal end of the clotting device at a selected position. In one form, the inflatable means 32 comprises a flexible sleeve located within a recessed area 44 at the distal end 24 of the tube 22. Each end of the sleeve is adhered or bonded to the surface of the tube, within the recessed area, to define an inflatable balloon portion therebetween. Any suitable solvent, adhesive, or the like may be used to adhere or bond the sleeve to the tube. Inflation aperture 29 extends through the wall of the tube, to provide a fluid flow path between the inflation lumen and the unadhered portion of the sleeve, to permit inflation of the balloon. The sleeve and recessed area preferably have the same length and the recessed area is preferably recessed an amount equal to the thickness of the sleeve, so that the exterior surface of the tube will be smooth and essentially uninterrupted after the sleeve is attached. The surface of the balloon and the distal end of the tube may be treated with any suitable release agent so as to prevent breaking of any clot that has formed when the inflation means is deflated and the device eventually withdrawn from the patient.

Although the inflation means may also be used to apply the wound treating agent, as described in more detail later, in this embodiment, to treat a wound and particularly to assist in forming a blood clot at the site of the vessel aperture, a quantity of treating or clotting agent 34 is preferably located in the second lumen 30, for ejection onto the vessel opening or wound. When the treating agent is a clotting agent, it may be any of the suitable clotting agents presently commercially available. For example, the clotting agent 34 may be a thrombin agent. A thrombin agent is frequently used as a topical treatment by vascular surgeons to stop surface bleeding after a large incision is made in the body. By dispensing thrombin agent onto an aperture in an artery, bleeding from the aperture can be reliably hastened and stopped, reducing the risk of a hematoma, and eliminating the need for an overnight stay in the hospital. The treating agent, which is preferably in foam, powder, or gel form, may be pre-filled into the second lumen during manufacture or may be inserted into the second lumen at the time of the procedure.

The treating agent is deposited at the site of the aperture or wound from the distal end of the tube 22. The means, generally at 36, for dispensing the treating agent 34 is preferably a plunger 38, as shown in FIGS. 3 and 4. The plunger 38 has a distal end, generally at 46, and a proximal end, generally at 48. A rod 50 extends between the distal and proximal ends of the plunger. A piston or grommet 52 is located at the distal end of the rod 50 and a thumb rest 54 is provided on the proximal end. By advancing the plunger 38, the piston 52 forces the agent 34 from the distal end 24 of the tube 22. Calibrations may be provided on the rod and/or tube to provide an indication of the amount of agent dispensed and the rate of dispensing. In FIG. 3, the piston 52 of the plunger 38 is nearer the proximal end 26 of the tube 22 and has not yet been advanced towards the distal end 24 of the tube 22. FIG. 4 illustrates the piston 52 being advanced towards the distal end 24 of the tube 22, ejecting the agent 34. FIG. 4 also depicts inflation of the inflation means 32 by injection of a fluid 40 (which may be gas or liquid, but is preferably liquid such as sterile water) into the inflation lumen 28 to retain the distal end 24 at some selected location in the patient.

Figure 6:
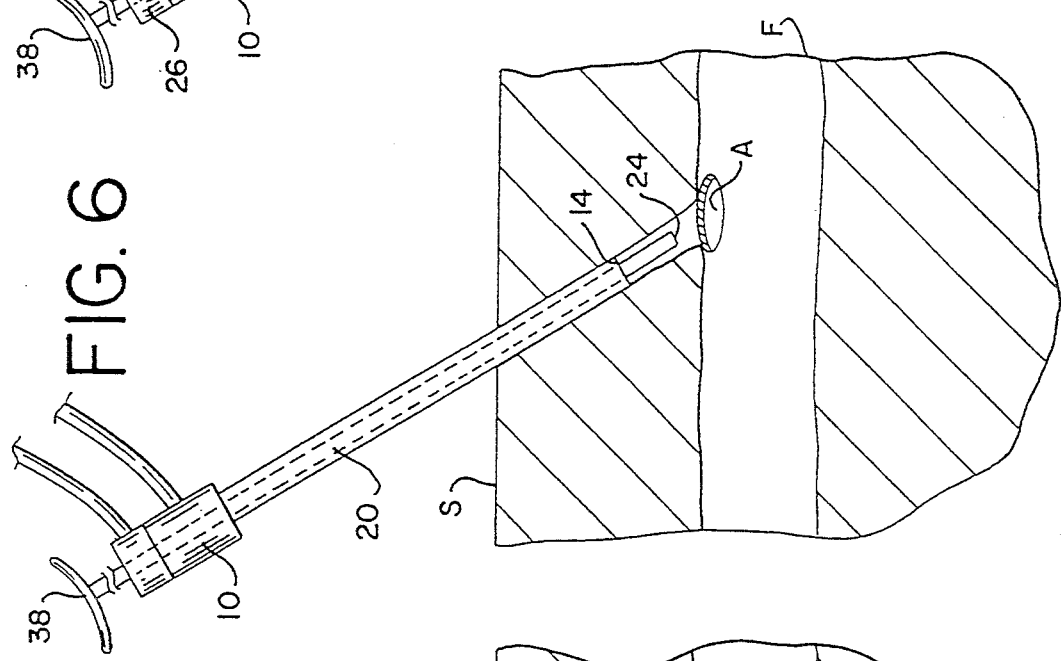
FIG. 6 is a side view depicting one of the steps of the method of the present invention, utilizing the wound treating or clotting device depicted in FIGS. 2, 3, and 4, where the sheath introducer of FIG. 5 has been retracted from the blood vessel and the wound clotting device has been inserted into the introducer.
Figure 7:
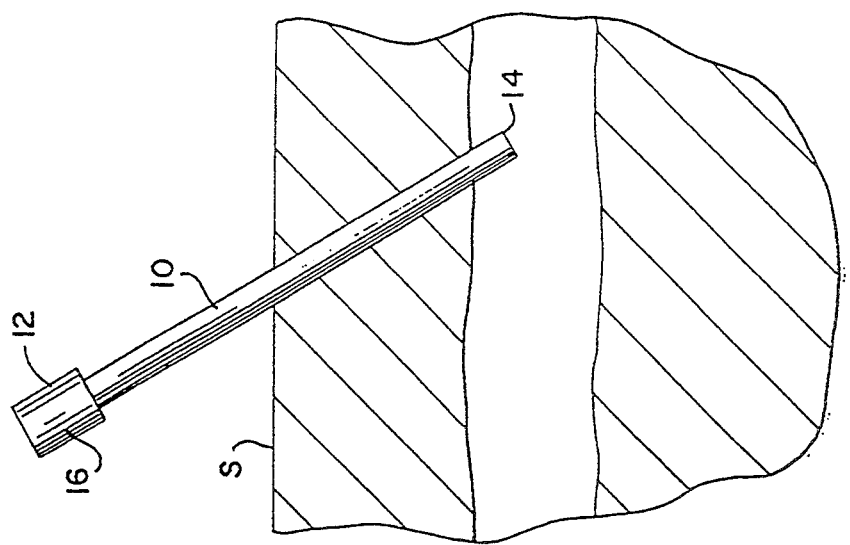
FIG. 7 is a side view depicting another of the steps of the method of the present invention where the treating or clotting device of FIGS. 2, 3, and 4 is utilized to dispense clotting agent onto an aperture in a blood vessel.

Use of this embodiment of the present invention in forming a vascular clot is depicted diagrammatically in FIGS. 5–7. FIG. 5 shows an introducer cannula, for example the sheath introducer 10, which previously has been inserted through the skin surface into a femoral artery F, and following removal of the particular medical device.

As shown in FIG. 6, the introducer 10 is retracted out of the artery F, leaving an aperture or opening A in the wall of the artery F. The introducer 10 is retracted until it is out of the artery and spaced from the artery (although it is not completely removed, and remains in the proximity of the artery). The wound clotting device 20, as described above, is then inserted through the valve 12 of the introducer 10 and into the introducer 10. The device 20 is then advanced through the introducer 10 until the distal end 24 of the clotting device 20 extends beyond the distal end 14 of the introducer 10 and is adjacent to the aperture A in the artery F. To assure that the device is advanced the proper amount, the device may be of a selected length for each particular brand of introducer sheath used, or have indicia along the length of the tube 22 to indicate how far it should be advanced for each particular brand or style of introducer sheath.

As shown in FIG. 7, the inflatable means 32 is then inflated to retain or hold the distal end 24 of the clotting device 20 adjacent to the artery F. Accordingly, the distal end 24 cannot be pushed into the aperture A or pulled away from the aperture A. The plunger 38 is then advanced and the clotting agent 34 is dispensed from the distal end 24 of the tube 22 and onto the aperture A of the artery F. The clotting agent 34 will greatly hasten clotting and assist in preventing further bleeding from the aperture A.

The inflatable means 32, on the distal end 24 of the clotting device 20, may also be manually pressed and held against the aperture A in the artery F to assist clotting. This step is done after the retention means 32 has been inflated and the clotting agent has been dispensed onto the aperture A. By pressing the inflatable retention means 32 against the artery F, pressure is put on the aperture A to assist the clotting agent 34 in clotting the bleeding from the aperture A. Finally, after sufficient time for clotting has elapsed, the retention means 32 is deflated and the clotting device 20 and the introducer 10 are withdrawn from the patient's body, leaving no substantial amount of foreign material within the patient's vascular system.

An alternate embodiment of the wound treating device of the present invention is shown in FIGS. 8-15. The device of FIG. 8 includes an elongated tube 56, preferably extruded of suitable plastic material, which extends between a proximal end portion 58 and a distal end portion 60. The tube also includes a hollow bore or lumen 62, which extends fully between the proximal and distal end portions.

For dispensing a treating agent at the site of a wound and for retaining the device in the vicinity of the wound, a flexible membrane 64 is attached at the distal end 60 of the tube 56. The membrane preferably has the shape of a short balloon, open at one end for attachment to the tube and closed at the other end. Other shapes, however, may also be used without departing from the present invention.

The membrane is preferably made of a flexible plastic material of the type which is compatible with medical applications, such as silicone, polyethylene, polypropylene, polyurethane, latex or the like. Prior to use, the balloon is located in an inverted or invaginated position within the distal end of lumen 62. When in this position, the membrane forms a pocket, into which treating agent 65 may be placed. The treating agent 65 may be of any desired material, such as an antibiotic, thrombin or clotting agent, in powder, gel or other suitable form. The treating agent may be pre-inserted into the tube during the manufacturing process or may be added to the tube at the time of use. If pre-inserted during manufacture, a removable hermetic seal 66 may be provided by adhesive bond or other suitable attachment over the distal end of the tube to preserve the treating agent against degradation during storage. The seal may be removed prior to use, or may be made of a material which dissolves upon contact with liquid such as bodily fluids or blood encountered when inserting the device into position adjacent the wound site.

Figure 9:
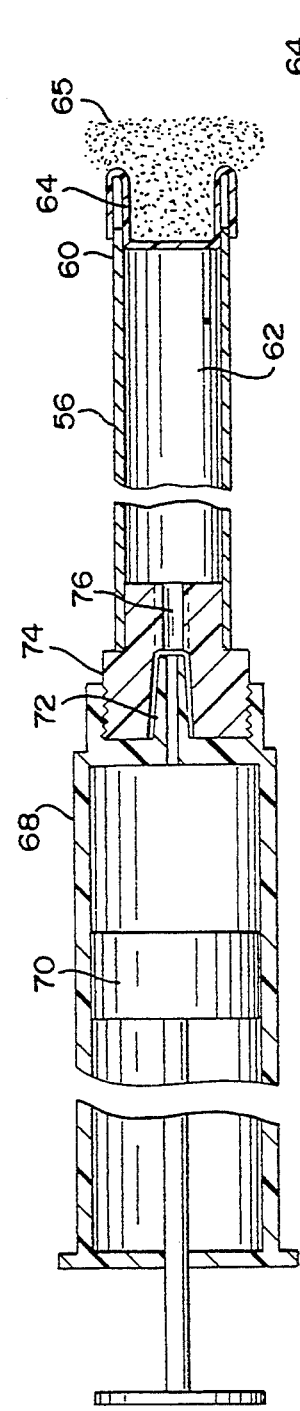
FIG. 9 is an enlarged cross-sectional view showing the wound treating device of FIG. 8 in an advanced stage of dispensing a treating agent.
Figure 10:
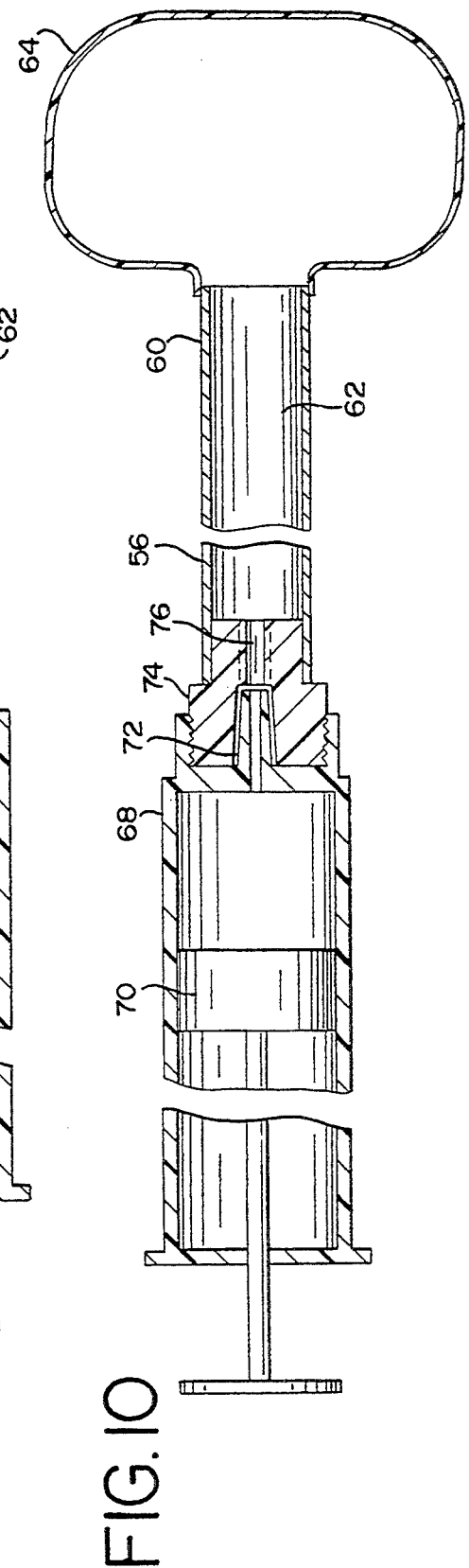
FIG. 10 is an enlarged cross-sectional view showing the embodiment of FIG. 8 after all the treating agent has been dispensed and the membrane inflated.

To dispense the treating agent, as shown in FIGS. 9 and 10, the lumen 62 is pressurized by liquid or gas to push or inflate the membrane, causing it to expel the treating agent from the distal end of the lumen. Preferably a syringe of typical construction having a barrel 68, plunger or piston 70 and male luer fitting 72, is used to pressurize the lumen. To accommodate such a syringe, a female luer connector fitting 74 is provided at the proximal end of the tube 56. The fitting 74 includes a through passageway 76 which directly communicates at one end with the lumen and communicates at the other end with a standard tapered female luer connector. Although a luer-slip or luer-lock connection may be used, the illustrated fitting 74 has external threads for threaded engagement with the syringe (to provide a luer-lock arrangement) which prevents inadvertent separation of the syringe and tube.

Figure 8:
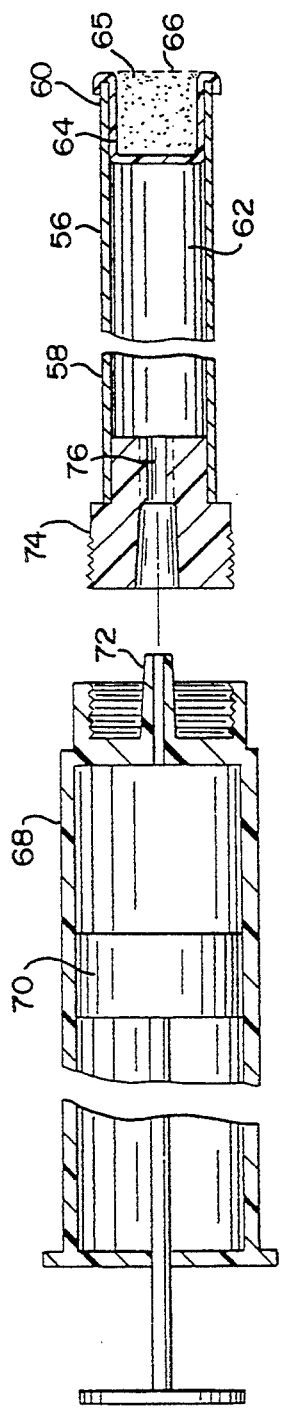
FIG. 8 is an enlarged cross-sectional view of the proximal and distal end portions of an alternate wound treating device, having an expandable retention and dispensing means in the form of a balloon membrane at the distal end.

FIGS. 11-15 illustrate how the alternative device shown in FIGS. 8-10 may be used in treating a wound and, in particular, in assisting clotting of an opening in a blood vessel F. As shown in FIGS. 11-14, the device may be used without an introducer sheath, although an introducer sheath is normally preferred. The distal end of the tube is inserted through the skin S to the site of the opening or aperture A in the blood vessel F. As noted above, the tube 56 may be inserted through an introducer or it may be introduced through an opening in the skin provided by another instrument. The tube is inserted until the distal end is generally adjacent to the wound.

Figure 12:
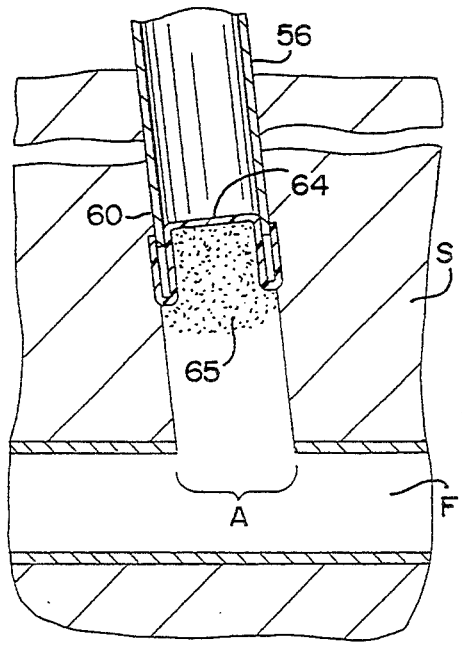
FIG. 12 is a cross-sectional view of the treating device of FIG. 8 showing clotting agent being dispensed at the aperture of a blood vessel.
Figure 13:
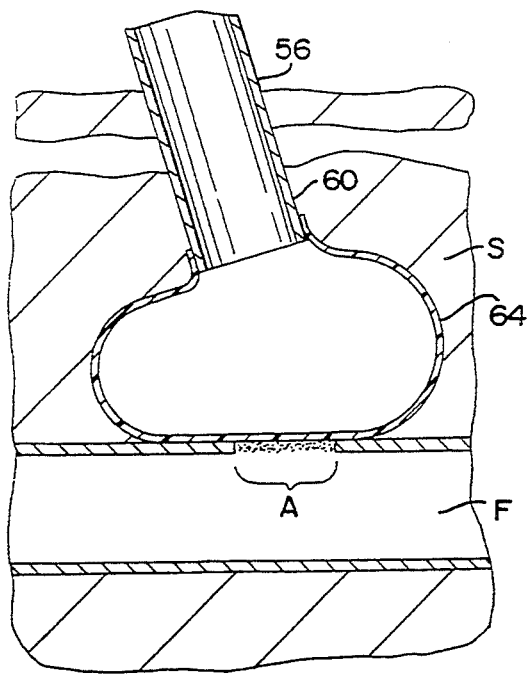
FIG. 13 is a cross-sectional view of the treating device of FIG. 8 showing the membrane fully inflated after the clotting agent has been dispensed, and being held against the wound.

The lumen of the tube is then pressurized, such as by high pressure liquid or air preferably liquid, injected into the lumen from a syringe. The pressure forces the membrane outwardly, expelling the treating agent at the site of the wound, as shown in FIG. 12. Continued application of pressure causes the membrane to expand to completely expel the treating agent 65 and form a balloon-like projection, as shown in FIG. 13, which has several advantages. First, when fully inflated, the balloon-like projection serves to retain the tube in the desired position relative to the site of the wound. When used to assist clotting in blood vessels, the balloon-like projection further helps block blood flow from the vessel and applies pressure against the vessel opening. The pressure applied by the balloon may also be supplemented manually by user force exerted on the proximal end of tube 56.

Figure 10A:
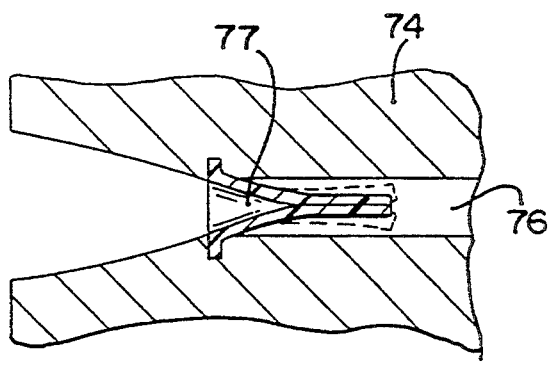
FIG. 10a is an enlarged cross-sectional view of a one-way valve that may be used to maintain inflation of the membrane.
Figure 11:
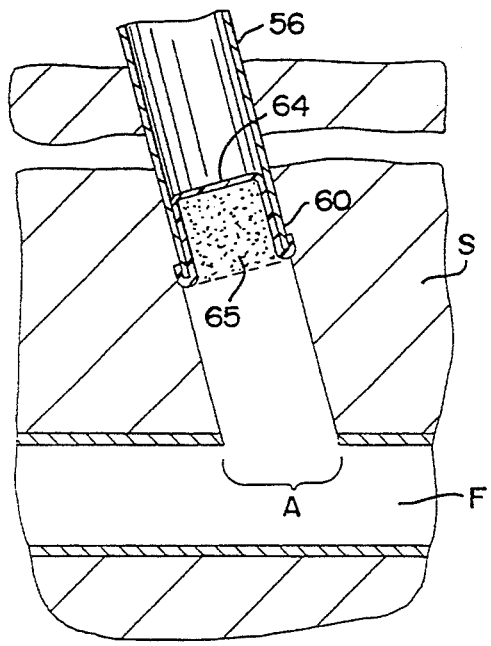
FIG. 11 is a cross-sectional view of the distal end of the treating device in FIG. 8 inserted into the skin, approaching a blood vessel.

To avoid the need to maintain pressure on the syringe, the wound clotting device may include a releasable one-way inflation valve positioned, for example, in the inflation lumen which would allow syringe to be removed and the balloon to remain inflated in a position against the hole in the artery to block blood flow without a medical attendant being present. Such a valve could be of any suitable known type, such as a flexible duckbill or diaphragm valve 77 located in the passageway 76 of luer fitting 74 as is illustrated, for example, in FIG. 10a—depicted in the closed position in solid lines and in the open position in dashed lines.

Figure 14:
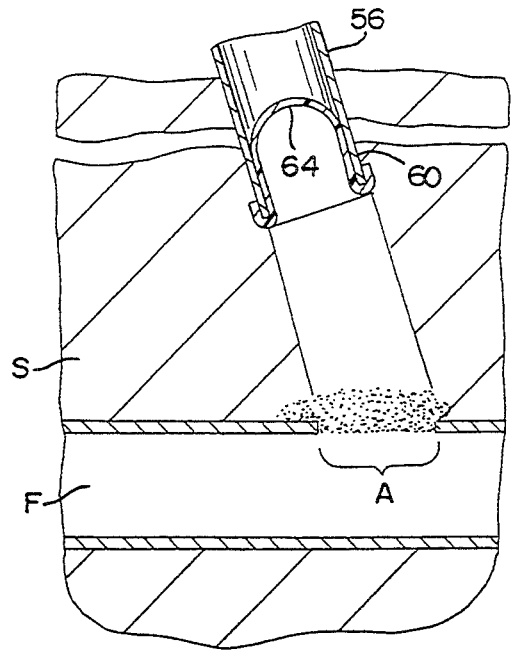
FIG. 14 is a cross-sectional view of the wound clotting device of FIG. 8 showing the wound clotting device being removed from the aperture after deflation of the membrane.
Figure 17:
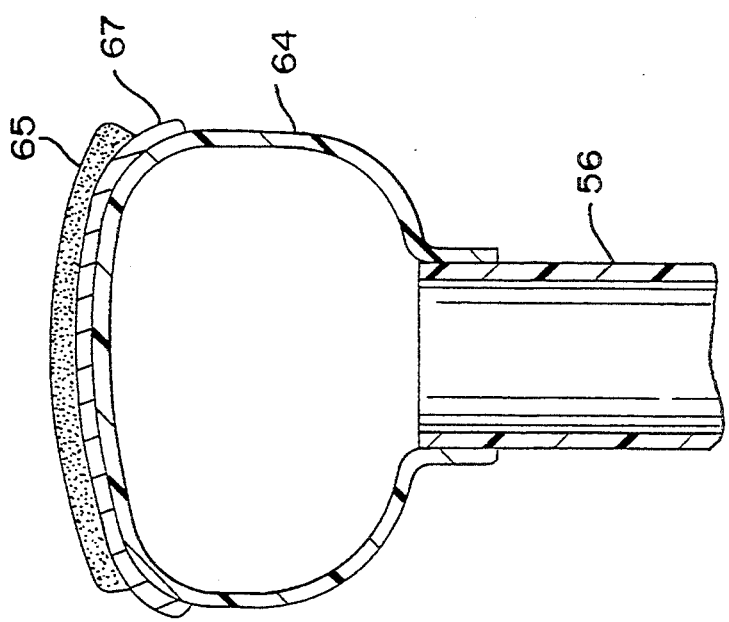
FIG. 17 is a cross-sectional view showing the inflated membrane in a balloon-like shape having a release agent and a treating agent applied.
Figure 20A:
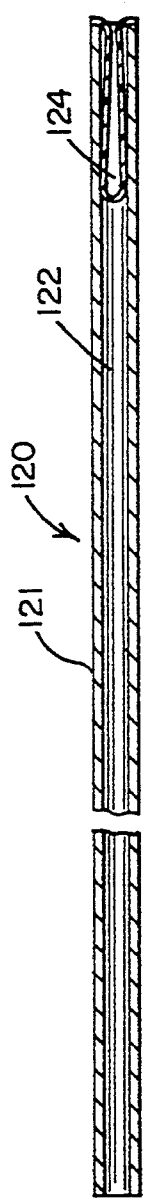
FIG. 20A is a cross-sectional view of the flow control device, with the membrane in a deflated and retracted position, that forms a part of the present invention.
Figure 20B:
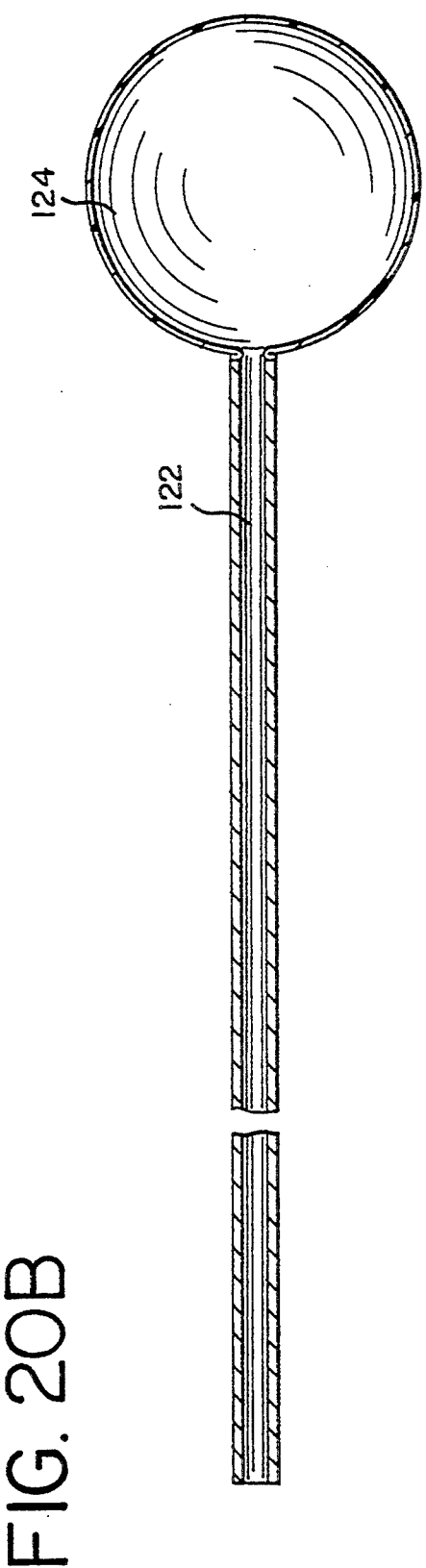
FIG. 20B is a cross-sectional view of the flow control device, with the membrane in an inflated position, that forms a part of the present invention.

After the treatment is completed, the balloon is deflated and the tube 56 withdrawn, as shown in FIG. 14. To allow release of the membrane from the wound, the membrane is preferably coated with a non-stick release agent which will be described in more detail in reference to FIGS. 16-18.

Figure 15:
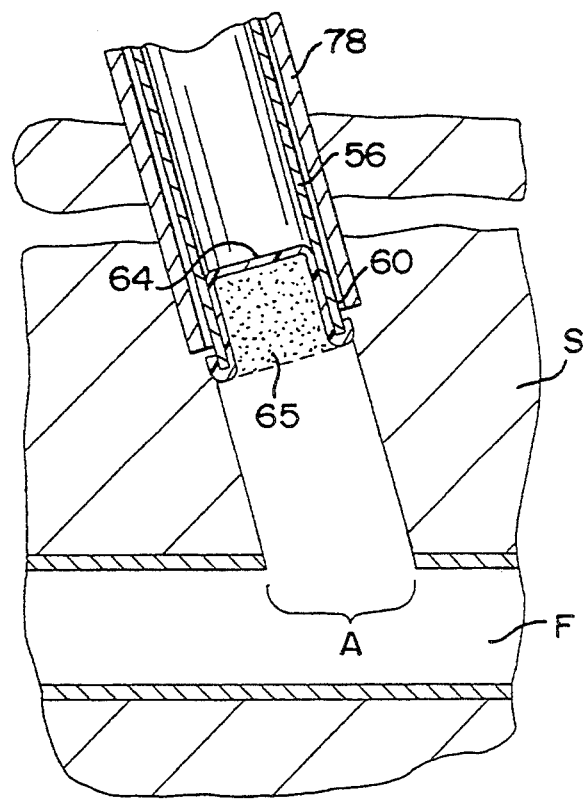
FIG. 15 is a cross-sectional view of the wound clotting device of FIG. 8 used in conjunction with a sheath introducer.

FIG. 15 depicts use of the alternate device in combination with an introducer sheath 78. When used with an introducer sheath, the tube 56 should be of sufficient length to extend beyond the distal end of the sheath to permit ejection of the treating agent at the wound site and to permit inflation of the membrane to form the balloon-like projection. Otherwise, the construction and operation of the alternate device with an introducer sheath is essentially as described above. Of course, when used with an introducer sheath which extends into the wound itself, e.g., into an access opening in a blood vessel, the sheath is normally withdrawn from the wound before the tube 56 is moved through the distal end of the sheath to dispense the treating agent.

FIGS. 16A–16C depict a method for applying the desired release agent and treating agent to the surface of the membrane 64. First, the membrane 64 is expanded to a balloon-like shape. The membrane is then dipped or inserted into a container containing a release agent 67, for example, a moisture activated release agent, such as a starch. The thickness of the release layer depends on the material chosen and the viscosity of the material at the time of application. The thickness is also dependent on the speed of hydration, which is a function of the mass of the release agent and the exposed surface area. It is presently believed that the preferred thickness of the release agent for a vascular wound, such as the incision in a blood vessel made for angiographic procedures, is approximately 10–50 mils.

Figure 18:
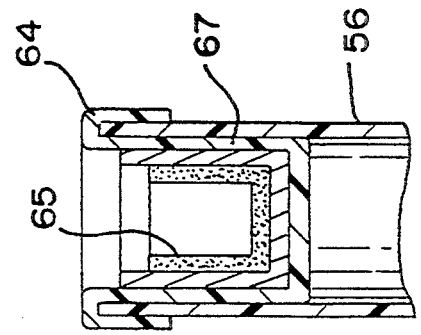
FIG. 18 is a cross-sectional view of the membrane, the release agent and the treating agent positioned within the tube.

The portion of the expanded membrane covered by the release agent is then placed in contact with a treating agent 65. A non-stick surface 69 such as Teflon material is preferably used to support the treating agent, and the inflated balloon is brought into contact with the treating agent so as to allow the agent to adhere to the surface, over the release agent. After the material on the membrane is dry as shown in enlarged dimension, for example, in FIG. 17, the membrane is drawn, as by suction, into an invaginated position within the tube as shown in FIG. 18.

Alternatively, the membrane 64 may itself be made of a material which has thrombogenic qualities, eliminating the need for a separate clotting agent. Specifically, the membrane could be made of a material having a specific activity which promotes clotting. It is understood that latex and some commercial grades of silicon rubber are naturally thrombogenic and promote clotting. Alternatively, other balloon materials, such as polyamide or PET, may be subjected to radiation or chemical treatment to increase surface activity to enhance clotting.

A further alternative embodiment of the present invention is depicted in FIGS. 19A–D. The embodiment of a wound treating device shown there has a detachable membrane, which may be left adjacent to the wound while the remainder of the device is removed. This embodiment comprises a plastic tubular portion 56 having a distal end 57, a proximal end 58 and a lumen 62 extending therebetween. A fitment 82 is carried at the proximal end of the tubular portion 56 and an inflation cannula 84 extends from the fitment, through the tubular portion to approximately the distal end 57 thereof.

More particularly, the fitment 82 is preferably of rigid molded plastic construction with a hollow distal end portion 86 sized for slidably receiving the proximal end 58 of the tubular portion 56 therein. A female luer taper bore 88 is provided at the proximal end of the fitment for receiving the standard male luer fitting of a syringe or similar pressurization means 90. Cannula 84 is coaxially and fixedly mounted within the fitment in communication with the female luer bore, and extends through the hollow distal end of the fitting and through the tubular portion 56.

The proximal end of the tubular portion 56 is attached to the fitment in a manner which permits at least limited axial movement of the tubular portion relative to the fitment and cannula. In the illustrated embodiment, the proximal end of the tubular portion has an enlarged, radially extending flange 92 slidably received within the open distal end of the fitment. Inturned end flange 94 of the fitment retains the proximal end of the tubular portion within the fitment and prevents inadvertent withdrawal of the tubular portion from the collar. As assembled, the proximal end flange 92 of the tubular portion is slidable between the inturned end flange 94 and internal shoulder 96 in the open end of the fitment.

The proximal end of the fitment 82 is preferably threaded at 98 for making a luer-lock connection with the syringe 90 or such other means as is desired for inflating the membrane. Alternatively, the syringe may be pre-attached to the collar. In either situation, the syringe or the collar may also include a pressure-limiting aperture 100 (shown, for example, in the syringe) which limits the pressure that may be applied to the inflation membrane.

In accordance with this embodiment of the present invention, the membrane 64 may be separated from the tubular portion 56 after inflated at the wound site. This is achieved by providing a piercable, resealable portion 102 of the membrane removably positioned at a location within the distal end of tubular portion 56, and by defining a pressurization chamber 104 within the tubular portion proximal of the membrane. An inflation passageway such as in the form of the cannula 84 is provided in the tubular portion, and is of sufficient length to extend, if desired, through the pressurization chamber and through the piercable, resealable portion 102 of the membrane. When extending through the piercable portion of the membrane, the membrane may be expanded by passage of pressurized liquid or gas through the inflation passageway. After inflation, the cannula may be withdrawn into the pressurization chamber 104, which is defined in part by the partition or plug 106, where the pressurization by injection of liquid or gas discharges or expels the membrane from the distal end of the tubular portion so that the tubular portion may be withdrawn, leaving the inflated membrane at the wound site.

This may be achieved with the illustrated embodiment wherein the membrane is sealed to the piercable portion 102. Piercable portion 102 is positioned within the distal end of the tubular portion. The diameter of the piercable portion 102 is slightly larger than the inside diameter of the lumen so as to be frictionally retained therein but expellable with pressure. The piercable portion 102 may be of any suitable material biocompatible such as silicone or may be made of a material which eventually dissolves or decomposes upon contact with bodily fluids.

As shown in FIG. 19A, the piercable portion 102 is preferably located at sufficient distance from the distal tip end portion of the tube so that the membrane 64 may be positioned in the invaginated position with the distal end of the tube, leaving a space between the piercable portion 102 and the invaginated membrane to reduce the chance of inadvertent membrane puncture when the cannula 84 pierces the piercable portion.

More particularly, the operation of the illustrated device with detachable membrane is most easily described in two steps. The first step includes expanding the membrane and the second step includes detaching the membrane, including piercable, resealable portion 102. To allow for expanding the membrane of the wound treating device, the tubular portion including flange 92 is positioned within the fitment in a first position, as shown in FIG. 19A, where flange 92 is positioned adjacent shoulder 96 of the fitment. When in the first position, the cannula 84 extends through the piercable portion of the membrane such that the end of the cannula is positioned within the interior of the membrane. As pressure is applied by way of the syringe, the membrane is expanded to a balloon-like shape outside the tubular portion, as shown in FIG. 19B, simultaneously applying any associated treating agent to the wound and applying pressure to the wound in the same manner as described in the prior embodiment.

In order to detach the membrane from the device, the tubular portion is moved axially relative to the syringe and fitment to a second position as shown in FIG. 19C such that the flange 92 of the tubular portion is near or abuts the inturned flange 94 of the collar. In the preferred embodiment, the fitment is shaped (for example, with an internal detent) such that when the tubular portion is moved to the second position, the sliding flange 92 in place. Preferably, the movement of the tubular portion is accomplished by manually retracting the syringe and fitment slightly while holding the tube fixed. Although the axial movement of the tube is accomplished in this embodiment by sliding the tube relative to the fitment, relative axial movement could also be achieved by rotation if the fitment and tube were threadedly instead of slidably attached.

When the tubular portion is in the second position, the end of the cannula is positioned within the chamber 104 defined within the tube between partition or plug 106 and piercable, resealable portion 102.

The pressurization chamber 104 is designed to allow the membrane 64 including piercable portion 102 to be expelled when the chamber is pressurized. Specifically, partition or plug 106 is securely attached to the tube. When pressure is applied to chamber 104 by way of the syringe, the membrane including the piercable portion 102 is forced out or expelled, as shown in FIG. 19D. This allows the tubular portion to be withdrawn, leaving the inflated membrane in the treating position at the wound site and permits any attending medical personnel to resume other duties. If constructed from biodegradable material, no subsequent deflation or removal is even required A further improved embodiment of the present invention comprises a wound treating device such as previously shown and described in FIGS. 1-7 and 8-15, for example, but further containing an additional lumen for receiving a flow control device that is partially positioned within the blood vessel for controlling flow through the aperture. As described in more detail below, the flow control device, in its illustrated embodiment, comprises a hollow tubular portion adapted to be received within the additional lumen, and a membrane attached to one end of the tubular portion to define a balloon-like portion within the vessel when inflated.

FIGS. 20-24 illustrate this further embodiment of the present invention. The illustrated embodiment shown in FIG. 20A comprises a flow control device 120 including a tubular member 121 of suitable plastic material or the like having a coextensive interior passageway 122. Elastic membrane 124, in the shape of a pouch and capable of repeated inflation and deflation without appreciable effect on the integrity of the walls of the membrane, is sealably attached at the distal end of the tubular member 121 to form a balloon which is inflatable by the introduction of pressurized fluid through the passageway 122. FIG. 20B shows the membrane 124 in an inflated mode. Prior to inflation, the membrane is preferably disposed within the distal end of the interior passageway 122 for ease of insertion into the vessel, as described more fully below.

Figure 21A:
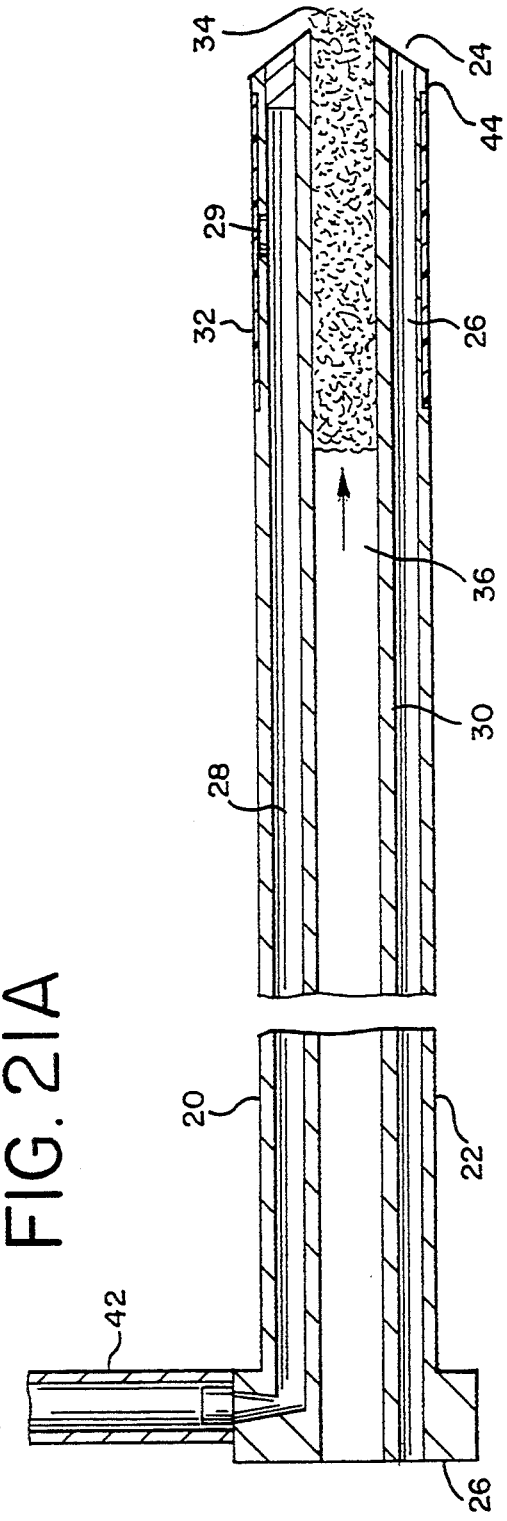
FIG. 21A is a cross-sectional view showing the proximal and distal ends of an alternate wound treating device of the present invention.

FIG. 21A shows a modified version of the wound treating device 20, previously described in FIGS. 1-7, in which a third lumen 126 is provided between the proximal and distal ends of the elongated tube 22. The third lumen 126 is of sufficient diameter to slidably receive the flow control device 120, and the relative lengths of the lumen 126 and device 120 are such that the distal end of the flow control device 120, containing the inflatable membrane 124, may be positioned at or beyond the distal end of the wound treating device 20. The flow control device 120 has, at its proximal end (not shown), a valve, such as the duck bill type valve shown in FIG. 10a or conventional stopcock, to prevent deflation of the inflatable membrane 124 after pressurized fluid, such as sterile water, has been introduced by any suitable means, such as by the syringe as described in FIGS. 9 and 10, supra.

Figure 21B:
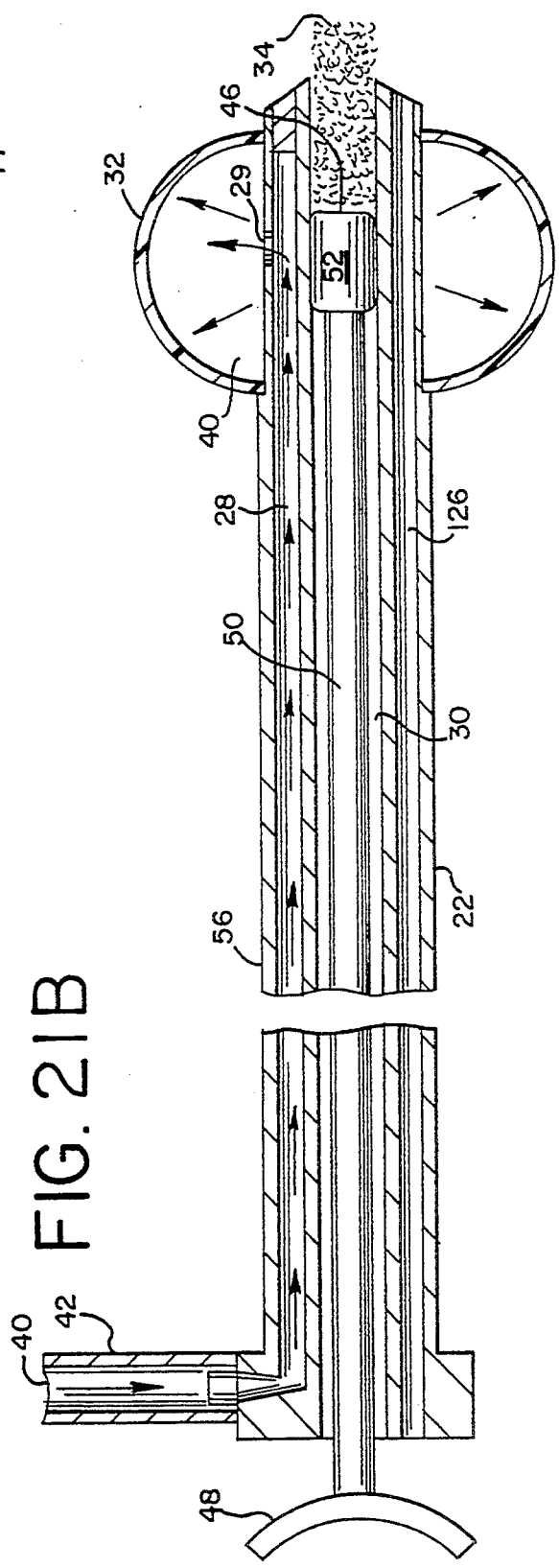
FIG. 21B is a cross-sectional view of the wound treating device of FIG. 21A with the inflatable means being inflated and a treating agent being dispensed.

FIG. 21B illustrates wound treating device 20 with a modified version of the retention means (balloon membrane) 32 in an inflated mode in the wound treating device 20 having a third lumen 126 formed therein. The placement of the third lumen 126 within the walls of the tube 56 is such that the membrane 124 of the flow control device, when inflated, will not interfere with the retention means 32 when it is also inflated, as illustrated and described below.

Figure 22E:
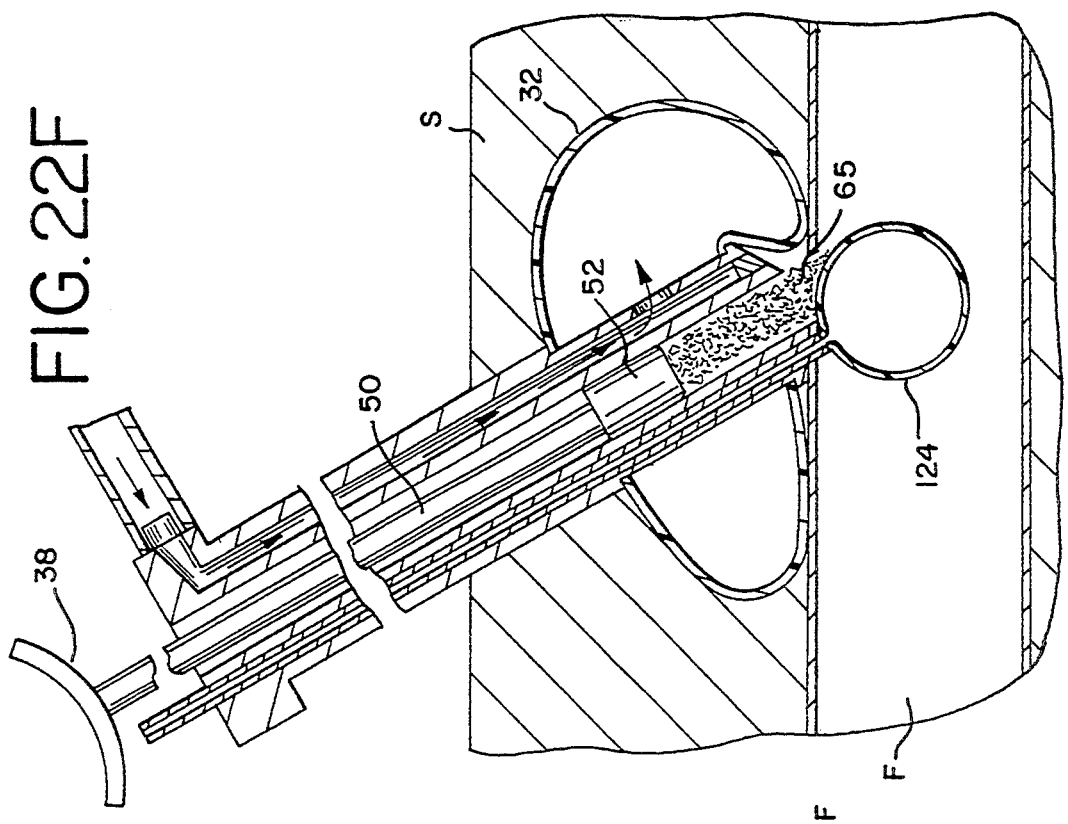

FIGS. 22A-F diagrammatically illustrate the additional embodiment of FIGS. 20-21 as it may be actually used. In FIG. 22A, the sheath introducer 10 is advanced through the patient's skin S to the artery F. As discussed earlier, the sheath introducer 10 is normally inserted at the beginning of the angiographic or angioplasty procedure, and remains in position after the angiographic or angioplasty catheter is removed. The flow control device 120 is then inserted into the lumen of the introducer 10 until the distal end of the flow control device 120 is positioned within the artery F adjacent the site of the wound (FIG. 22B). During this step, the balloon membrane 124 is preferably, but not necessarily, in an invaginated position to permit the placement of the flow control device 120 within the artery F.

As shown in FIG. 22C, the balloon membrane 124, at the distal end of the flow control device 120, is then inflated with sterile water or other fluid using the valve means (not shown) so as to cover or occlude the wound in the wall of the artery F. The inflated balloon membrane 124 is drawn against the opening in the artery F by gently pulling the tubular portion 121 back to block or substantially occlude the aperture or opening in the vessel made by the introducer 10. The introducer 10 may then be removed.

FIG. 22D illustrates the next step in the procedure utilizing the alternative embodiment depicted in FIGS. 20 and 21. As shown there, the flow control device 120 helps to locate and guide the wound treating device into position in the vicinity of the aperture of the artery. Specifically, the tubular portion 121 of the flow control device 120 is inserted into the third lumen 126 of the wound treating device 20. The wound treating device 20 is then slid down the tubular portion until the distal end of the wound treating device 20 is generally in the vicinity of the opening or aperture in the artery wall F, which is at least partially occluded by the inflated balloon membrane 124.

As shown in FIG. 22E, the inflatable retention means 32 is then inflated in the manner previously described in FIG. 4, supra, so as to securely position the wound treating device 20 and to allow application of pressure if desired, in preparation for the introduction of the hemostatic agent 65 to the wound site. The retention means 32 also serves to restrict blood flow from the vessel.

Figure 22F:
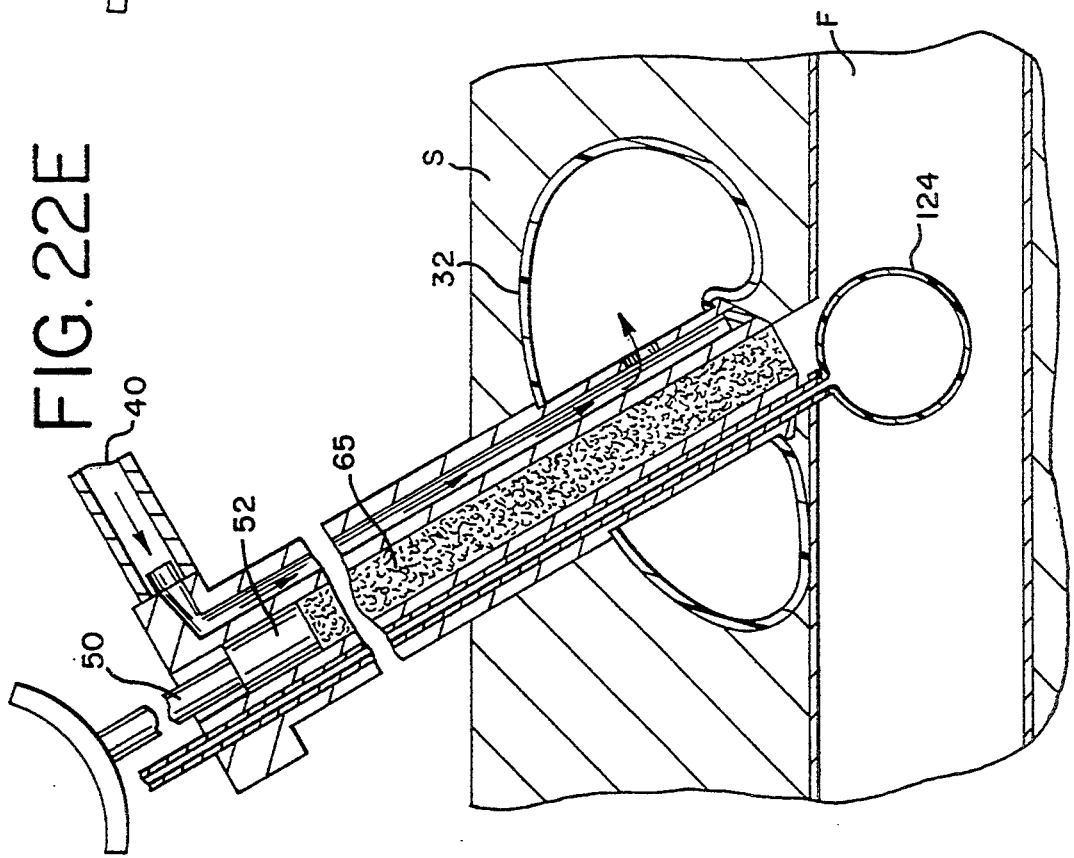

FIG. 22F illustrates the introduction of the clotting agent 65 directly to the site of the wound through the movement of the plunger 38, in the manner previously described and illustrated in FIGS. 3 and 4, supra. The inflated membrane 124, which at least partially occludes the vessel aperture, helps prevent the clotting agent from flowing into the vessel and helps maintain it between the balloon membrane 124 and the retention means 32. The treating agent 65, and the inflated balloon membrane 124 and retention means 32, together with the natural clotting process of the patient's body, act to stop the bleeding at the wound site. Alternatively, the balloon membrane 124 may be retracted before the introduction of the treating or clotting agent 65.

To assist the treater in removing the wound treating device 65 after the clot is formed, the device 20 may be treated with a coating or release agent on its surface so as to enable the easy removal of the wound treating agent while minimizing the probability of clot breakage during removal.

While not shown in FIGS. 21 and 22, the tubular portion 121 of the flow control device 120 may also be inserted into the second lumen 30 instead of into a third lumen 126. In the operation of this embodiment, the wound treating device 20 is slid down along the flow control device 120 until the distal end of the wound treating device 20 is generally in the vicinity of the artery wall F at which time the inflatable means 32 is inflated. The inflatable balloon membrane 124 of the flow control device 120 may then be retracted into the distal end of the flow control device 120, and the flow control device 120 withdrawn from the second lumen 20, or the balloon membrane may remain inflated within the vessel. A treatment or clotting agent may then be introduced via the second lumen 30 using a dispensing means, such as a plunger 38.

FIGS. 23A-C illustrate the alternative embodiment of the wound treating device 20 previously described in FIGS. 8–15, with the additional modification of the third lumen 126 formed within the walls of the elongated tube 56 (FIG. 23A). The flow control device 120, which has essentially the same construction as previously described, is adapted to be inserted into the third lumen 126 (FIG. 23B) such that the distal end of the flow control device 120 extends beyond the end portion of the elongated tube 56 and the treating agent 65. In this manner, the distal end of the elongated tube 56 may be positioned adjacent the wound site and outside the artery F, while the flow control device 120 is positioned adjacent the wound site and within the artery F.

FIGS. 23B and 23C, illustrate the inflation of flexible membrane 64, in the manner previously describe and illustrated in FIGS. 8–10, using pressurized liquid or air, which is introduced into the tube 56 by means of the plunger or piston 70. As the piston 70 moves forward, it inflates the flexible membrane 65 and ejects the treating agent 65, in the manner previously described and shown in FIGS. 8–15, onto the wound.

Figure 24A:
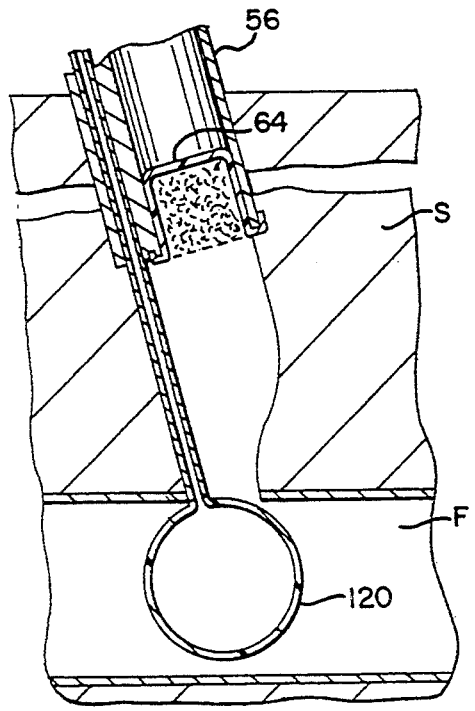
FIGS. 24A–D show, in sequential operative positions, the alternate embodiment of the wound treating device of FIG. 23.

FIGS. 24A–D illustrate this further embodiment of the invention as it may be used. As shown in FIG. 24A, the flow control device 120 extends beneath the opening in the wound into the artery F. After penetrating the artery F and inflating the balloon membrane 124, the tubular portion 121 of flow control device 120 is gently pulled backwards so that the balloon means 124 abuts and occludes the wound opening in the wall of the artery F. As described earlier, the distal end of the wound treating device is positioned generally adjacent to the opening in the artery F. The wound treating device is inserted over the tubular portion of the flow control device and into the incision leading to the wound site. The flexible membrane 64 of the treating device is maintained in a pocket, in which the treating agent may be located, as previously disclosed and described in FIG. 8.

Figure 24B:
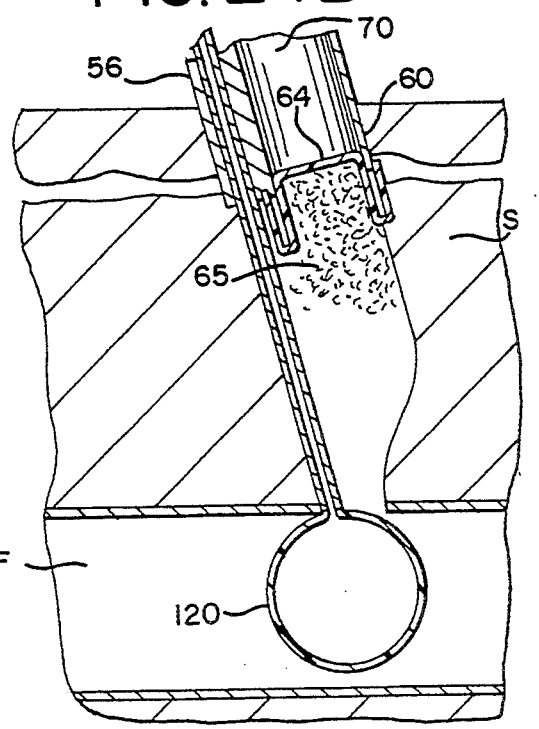

In the next step in the procedure as shown in FIG. 24B, the flexible membrane 64 is inflated by the insertion of air or fluid using the plunger 70, in the manner previously illustrated in FIG. 10 and described in the corresponding portion of the specification, thus pushing the treating agent 65 out the distal end of the tube 56 to the site of the wound in the artery F. The flexible membrane 64, the treating agent 65, and the inflatable balloon membrane 124 work together to bring about the cessation of bleeding in a faster and more efficient manner. As the inflated balloon membrane 124 occludes the wound, the treating agent 65 assists the body's natural clotting process, providing a more rapid closure of the wound. Alternatively, the balloon membrane 124 may be retracted before the introduction of the treating or clotting agent 65.

Figure 24C:
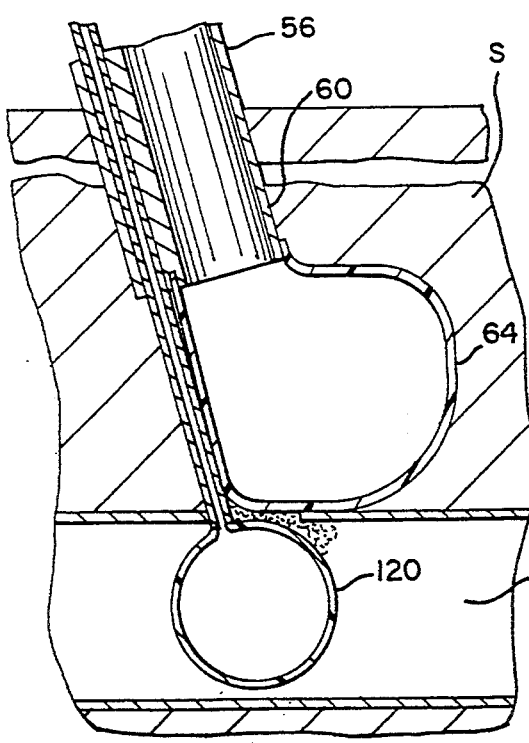

FIG. 24C depicts the flexible membrane 64 and the inflatable balloon membrane 124 in the inflated mode, with the treating agent 65 having been placed over the wound surface in the artery F. The inflated flexible membrane 64 secures the tube 56 in the desired position and allows pressure to be applied to the site if desired. The flow control device 120 is maintained against the inside surface of the artery F to block or substantially reduce the flow of blood; thus giving the treating agent and the patient's own clotting process the opportunity to close the wound.

Figure 24D:
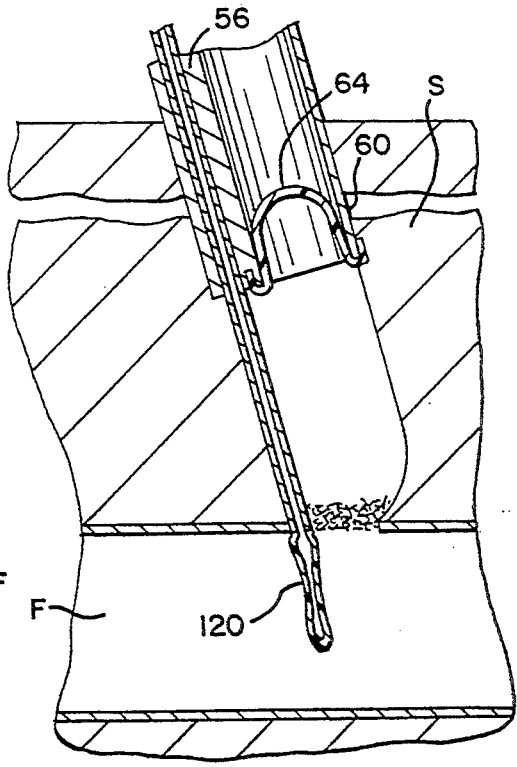

FIG. 24D illustrates the final step of the procedure following at the conclusion of the clotting process. After closure of the wound is substantially completed, the inflatable balloon membrane 124 is deflated by the removal of air or water through the valve means (not shown), such as the duckbill valve previously discussed. Similarly, the flexible membrane 64 of the treating device is deflated in the manner previously described, and retracted to the invaginated position within the tube 56. The treater may then retract the now deflated balloon membrane 124 through the elongated tube 120, and remove the tube 56 from the skin of the patient. A release agent or material may coat the membrane 124 and end of the elongated tube 120 to ease removal of the flow control device without breaking the clot. With the treating agent 65 assisting the natural clotting process occurring in the body, the wound is now closed in a much shorter time than previously obtainable using prior art technology.

Although the preferred construction of the alternate device is described above, various changes may be made without departing from the present invention. The features of the wound treating device and method of the present invention have been described in connection with the accompanying drawings for purposes of illustration and not limitation. It is intended that this application include those modifications, variations and additions that would be readily apparent to one of ordinary skill upon reading this description. Accordingly, for ascertaining the scope of the present invention, reference must be made to the appended claims.

We claim:

1. A wound treating device adapted to be positioned adjacent to an aperture in a blood vessel comprising:
an elongated tube having proximal and distal end portions, said tube comprising at least first and second lumens extending between said proximal and distal ends;
said first lumen adapted to receive a flow control device partially positioned within the blood vessel for providing local flow control at the aperture in the blood vessel;
a flexible membrane carried generally adjacent said distal end portion and movable between a retracted position and an inflated position to form a balloon-like projection at said distal end; and
a wound treating agent releasably pre-disposed within said elongated tube and releasable into the vicinity of the aperture in the blood vessel.

2. The wound treating device according to claim 1, wherein said wound treating agent is carried within said second lumen.

3. The wound treating device of claim 2, wherein said treating agent comprises a blood clotting agent.

4. The wound treating device of claim 1, wherein said membrane is positionable within said distal end of said second lumen to form a pocket for receiving said treating agent.

5. The wound treating device according to claim 1, wherein a release agent is disposed on said membrane.

6. The wound treating device according to claim 1, wherein said proximal end of said tube includes a connection site for communication with means for moving said membrane between said retracted position and said inflated position.

7. The wound treating device according to claim 1, wherein said balloon-like projection is of a size larger than the diameter of said tube.

8. The wound treating device of claim 1, wherein said membrane closes the distal end of said second lumen, whereby pressurization of said second lumen moves said membrane from the retracted position to the inflated position.

9. The wound treating device of claim 1, wherein said treating agent is disposed on the surface of said membrane.

10. The wound treating device of claim 1, further including a means at the proximal end of the second lumen for inflating said membrane.

11. The wound treating device according to claim 1, further comprising a flow control device, wherein said flow control device comprises a tubular portion disposed in said first lumen and a membrane attached to said tubular portion to define a balloon-like portion when inflated.

12. The wound treating device according to claim 11, further including means to inflate said membrane of said flow control device.

13. A wound treating device adapted to be positioned adjacent to an aperture in a blood vessel comprising:
a flow control device having a tubular portion including proximal and distal ends, and a membrane attached to said distal end of said tubular portion, wherein said membrane is inflatable to define a balloon-like portion;
a tube having proximal and distal end portions and comprising at least first and second lumens extending between said proximal and distal end portions;
said tubular portion of said flow control device disposed within said first lumen and said membrane being positionable within the blood vessel for providing local flow control at the aperture in the blood vessel;
a membrane carried adjacent said distal end of said tube and in fluid communication with said second lumen for inflation when pressurized fluid is introduced into said second lumen; and
a wound treating agent releasably pre-disposed within said elongated tube and releasable into the vicinity of the aperture in the blood vessel.

14. The wound treating device of claim 13, further comprising a third lumen extending between said proximal and distal end portions of said tube, and wherein said treating agent is carried within said third lumen.

15. The wound treating device of claim 14, further comprising means for ejecting said treating agent being operatively coupled to said third lumen so as to dispense said treating agent from the distal end of said third lumen.

16. The wound treating device according to claim 15, wherein said means for ejecting said treating agent is a plunger located within said third lumen.

17. The wound treating device according to claim 13, wherein said membrane of said tube is disposed on said distal end portion of said tube, said membrane being adhered to said tube at each end of said membrane to define an inflatable balloon portion which, when inflated, will hold said tube adjacent to the aperature in the blood vessel.

18. The wound treating device according to claim 13, further including means to inflate said membrane of said flow control device.

19. A wound treating device adapted to be positioned adjacent to an aperture in a blood vessel comprising:
an elongated tube having proximal and distal end portions, said tube comprising at least first, second and third lumens extending between said proximal and distal ends;
a localized flow control device positionable through said first lumen and aperture and positionable partially within the blood vessel for providing local flow control at the location of the aperture in the blood vessel;
an inflatable membrane carried generally adjacent said distal end of said tube and in fluid communication with said second lumen and disposed for inflation when pressurized fluid is introduced into said second lumen;
a wound treating agent releasably pre-disposed within said elongated tube and releasable into the vicinity of the aperture in the blood vessel; and
an ejector operatively coupled to said third lumen for ejecting said treating agent.

20. The wound treating device according to claim 19, wherein said ejector for dispersing said treating agent is a plunger located within said third lumen.

21. The wound treating device according to claim 19, wherein said membrane of said tube is disposed on said distal end portion of said tube, said membrane being adhered to said tube at each end of said membrane to define an inflatable balloon portion which, when inflated, will hold said treating device adjacent to the aperature in the blood vessel.

22. The wound treating device according to claim 19, wherein said flow control device comprises a tubular portion with proximal and distal end portions; and a membrane attached to said distal end of said tubular portion, wherein said membrane is inflatable to define a balloon-like portion.

23. The wound treating device according to claim 22, further including means to inflate said membrane of said flow control device.

24. A method for treating wounds comprising the steps of:
providing a flow control device including a tubular portion having a proximal end, a distal end and a lumen extending therebetween, and an inflatable membrane carried at said distal end of said tubular portion;
inserting said flow control device into an aperture in a blood vessel;
positioning the inflatable membrane of said flow control device within the blood vessel adjacent the aperture;
introducing a wound treating device along said tubular portion of said flow control device, said wound treating device including an elongated tube having proximal and distal end portions and at least first and second lumens extending therebetween, said first lumen adapted to receive said tubular portion of said flow control device and said second lumen communicating with a membrane carried adjacent said distal end of said wound treating device; and
inflating said membrane means of said wound treating device adjacent to the aperture in the blood vessel.

25. The method for treating wounds according to claim 24, further including a step of contacting a treating means at the aperture in the blood vessel.

26. The method for treating wounds according to claim 24, wherein the step of inserting a flow control device includes inserting a flow control device through an introducer cannula into the aperture in the blood vessel and removing said introducer cannula.

27. The method of treating wounds according to claim 24, wherein the step of inserting said flow control device includes expanding said membrane of said flow control device to a balloon-like projection.

28. The method for treating wounds according to claim 24, wherein said membrane of said wound treating device is carried generally adjacent said distal end portion and is positionable within the distal end of said second lumen and movable between a retracted position within said second lumen and an inflated position to form a balloon-like projection at said distal end.

29. The method for treating wounds according to claim 24, wherein said membrane of said wound treating device is disposed for inflation when pressurized fluid is introduced into said second lumen.

30. The method of treating wounds according to claim 24, wherein said membrane of said tube is disposed on said distal end portion of said tube, said membrane being adhered to said tube at each end of said membrane to define an inflatable balloon portion which, when inflated, will hold said treating device adjacent to the aperature in the blood vessel.

31. The method for treating wounds according to claim 24, wherein said wound treating device further includes a third lumen extending between said proximal and distal end portions of said elongated tube; and
a treating agent disposed within said third lumen.

32. The method for treating wounds according to claim 31, further including means for ejecting said treating agent being operatively coupled to said third lumen so as to dispense the treating agent from the distal end of said third lumen at the vicinity of the aperture in the blood vessel.

* * * * *